United States Patent
Duggan et al.

(10) Patent No.: US 8,916,133 B2
(45) Date of Patent: Dec. 23, 2014

(54) FLUORINATED 2-AMINO-4-(BENZYLAMINO)PHENYLCARBAMATE DERIVATIVES

(71) Applicant: SciFluor Life Sciences, LLC, Cambridge, MA (US)

(72) Inventors: Mark E. Duggan, Wellesley, MA (US); Takeru Furuya, Cambridge, MA (US); D. Scott Edwards, Bedford, MA (US); Ajay Purohit, Sudbury, MA (US)

(73) Assignee: SciFluor Life Sciences, LLC, Cambridge, MA (US)

( * ) Notice: Subject to any disclaimer, the term of this patent is extended or adjusted under 35 U.S.C. 154(b) by 10 days.

(21) Appl. No.: 13/801,634

(22) Filed: Mar. 13, 2013

(65) Prior Publication Data

US 2013/0287686 A1    Oct. 31, 2013

Related U.S. Application Data

(60) Provisional application No. 61/640,157, filed on Apr. 30, 2012, provisional application No. 61/697,690, filed on Sep. 6, 2012.

(51) Int. Cl.
| | | |
|---|---|---|
| A61K 51/00 | (2006.01) | |
| A61M 36/14 | (2006.01) | |
| C07C 271/28 | (2006.01) | |
| A61K 51/04 | (2006.01) | |
| C07B 59/00 | (2006.01) | |
| C07F 15/00 | (2006.01) | |
| C07D 213/75 | (2006.01) | |
| C07F 5/02 | (2006.01) | |

(52) U.S. Cl.
CPC ........... *C07C 271/28* (2013.01); *A61K 51/0406* (2013.01); *C07B 59/001* (2013.01); *C07F 15/006* (2013.01); *C07D 213/75* (2013.01); *C07F 5/025* (2013.01)
USPC ............... 424/1.89; 514/485; 560/27

(58) Field of Classification Search
CPC combination set(s) only.
See application file for complete search history.

(56) References Cited

U.S. PATENT DOCUMENTS

| | | | | |
|---|---|---|---|---|
| 5,384,330 A | * | 1/1995 | Dieter et al. | 514/535 |
| 6,348,486 B1 | | 2/2002 | Argentieri et al. | |
| 2008/0188561 A1 | * | 8/2008 | Vernier et al. | 514/546 |
| 2009/0326059 A1 | * | 12/2009 | Wu et al. | 514/486 |

FOREIGN PATENT DOCUMENTS

| | | | |
|---|---|---|---|
| EP | 1407768 A2 | | 4/2004 |
| WO | WO 0101970 A2 | * | 1/2001 |
| WO | WO 02/49628 A2 | | 6/2002 |
| WO | WO 02/080898 A2 | | 10/2002 |

OTHER PUBLICATIONS

Purser et al. Chem. Soc. Rev., 2008, 37, 320-330.*
Donohue et al. J. Label. Cmpd. Radiopharm. 2008, 51, 146-152.*
Choi, Y. M. et al, "A nine-step synthesis of [$^{14}$C]flupirtine maleate labelled in the pyridine ring", *Journal of Labelled Compounds and Radiopharmaceuticals*, 24(1):1-14 (1987).
Lee, E. et al., "A Fluoride-Derived Electrophilic Late-Stage Fluorination Reagent for PET Imaging", *Science*, 334(6056):639-642 (2011).
Patani, G.A. et al., "Bioisosterism: A rational approach in drug design", *Chemical Reviews*, 96:3147-3176 (1996).
Moon, B. S. et al., "Facile aromatic radiofluorination of [$^{18}$F]flumazenil from diaryliodonium salts with evaluation of their stability and selectivity", *Organic & Biomolecular Chemistry*, 9:8346-8355 (2011).

* cited by examiner

*Primary Examiner* — Michael G Hartley
*Assistant Examiner* — Sean R Donohue
(74) *Attorney, Agent, or Firm* — Cooley LLP; Ivor R. Elrifi; Heidi A. Erlacher

(57) ABSTRACT

The invention relates to fluorinated compounds and their use as anti-epileptic, muscle-relaxing, fever-reducing and peripherally analgesically acting medications and as imaging agents. Novel fluorinated 2-amino-4-(benzylamino)phenyl carbamate derivatives of ezogabine and pharmaceutically acceptable salts or solvates thereof and their use are described.

6 Claims, No Drawings

FLUORINATED 2-AMINO-4-(BENZYLAMINO)PHENYLCARBAMATE DERIVATIVES

RELATED APPLICATION

This application claims priority under 35 U.S.C. §119(e) to U.S. provisional application Nos. 61/640,157 and 61/697,690, respectively filed on Apr. 30, 2012 and Sep. 6, 2012, which are incorporated herein by reference.

BACKGROUND

Epilepsy is one of the most common chronic neurological disorders. It is commonly diagnosed after 2 or more unprovoked seizures separated by at least 1 day, and it affects approximately 50 million people worldwide. Epilepsy is a serious and potentially life threatening disease and patients with epilepsy have significantly increased morbidity, including closed head injury, fractures, burns, dental injury and soft tissue injury. Decline in or worsening of memory, cognition, depression and sexual function and other lifestyle limitations occur frequently in patients with epilepsy. Patients with epilepsy also have an increased risk of mortality compared to the general population.

Despite the fact that there are already approved pharmacologic agents to treat epilepsy, many patients are not adequately treated with currently available options. It is estimated that nearly a third of patients with epilepsy have either intractable or uncontrolled seizures or have significant adverse side effects secondary to medication limiting their ability to appropriately control their epilepsy with medication.

Ezogabine or retigabine, also known as ethyl N-[2-amino-4-[(4-fluorophenyl)methylamino]phenyl]carbamate is an anticonvulsant used as a treatment for partial epilepsies. Ezogabine works primarily as a potassium channel opener—that is, by activating KCNQ2/3 voltage-gated potassium channels in the brain. Ezogabine was approved by the FDA on Jun. 10, 2010 and is marketed as Potiga™ and Trobalt™. U.S. Pat. No. 5,384,330 and WO 01/01970 describe ezogabine and its use. The most common adverse events with ezogabine are central nervous system effects, particularly dizziness and somnolence. These side effects are typical for antiepileptic drugs. Occasional instances of urinary difficulty may require surveillance. Ezogabine is predominantly metabolized via glucuronidation. Its half-life is 8 hours.

Despite the beneficial activities of ezogabine, there is a continuing need for new compounds to treat epilepsy and other conditions ameliorated by KCNQ2/3 potassium channel opening.

Fluorine-18 compounds that bind to KCNQ2/3 voltage-gated potassium channels are also needed to non-invasively determine the functional status of the channels by positron emission tomograghy (PET). PET imaging of subjects suffering from epilepsy or other conditions ameliorated by KCNQ2/3 potassium channel opening may provide clinically important information related to diagnosis of the condition, appropriateness and dosing of treatment, as well as facilitating the clinical development of new treatments.

DETAILED DESCRIPTION OF THE INVENTION

For purposes of the present invention, the following definitions will be used (unless expressly stated otherwise):

The term "a compound of the invention" or "compounds of the invention" refers to a compound(s) disclosed herein e.g., a compound(s) of the invention includes a compound(s) of any of the formulae described herein including formulae A, I, II, III, or IV and/or a compound(s) explicitly disclosed herein. Whenever the term is used in the context of the present invention it is to be understood that the reference is being made to the free base, a deuterium labeled compound, and the corresponding pharmaceutically acceptable salts or solvates thereof, provided that such is possible and/or appropriate under the circumstances. The fluorine atom or atoms in the compounds of the invention are non-radioactive.

The term "an 18F compound of the invention" or "18F compounds of the invention" refers to a compound(s) disclosed herein e.g., an 18F compound(s) of the invention includes an 18F compound(s) of any of the formulae described herein including formulae V, VI, VII, VIII, or IX and/or an 18F compound(s) explicitly disclosed herein. Whenever the term is used in the context of the present invention it is to be understood that the reference is being made to the free base and the corresponding pharmaceutically acceptable salts thereof, provided that such is possible and/or appropriate under the circumstances. For 18F compounds of the invention that also comprise non-radioactive fluorine, the non-radioactive fluorine is designated as 19F.

The term "pharmaceutical" or "pharmaceutically acceptable" when used herein as an adjective, means substantially non-toxic and substantially non-deleterious to the recipient.

By "pharmaceutical formulation" it is further meant that the carrier, solvent, excipient(s) and salt must be compatible with the active ingredient of the formulation (e.g. a compound of the invention). It is understood by those of ordinary skill in this art that the terms "pharmaceutical formulation" and "pharmaceutical composition" are generally interchangeable, and they are so used for the purposes of this application.

Some of the compounds of the present invention may exist in unsolvated as well as solvated forms such as, for example, hydrates.

"Solvate" means a solvent addition form that contains either a stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. In the hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates are sesquihydrates, monohydrates, dihydrates or trihydrates. Equally suitable are the hydrates of salts of the compounds of the invention The invention also includes metabolites of the compounds described herein.

Physiologically acceptable, i.e. pharmaceutically compatible, salts can be salts of the compounds of the invention with inorganic or organic acids. Preference is given to salts with inorganic acids, such as, for example, hydrochloric acid, hydrobromic acid, phosphoric acid or sulphuric acid, or to salts with organic carboxylic or sulphonic acids, such as, for example, acetic acid, trifluoroacetic acid, propionic acid, maleic acid, fumaric acid, malic acid, citric acid, tartaric acid, lactic acid, benzoic acid, or methanesulphonic acid, ethanesulphonic acid, benzenesulphonic acid, toluenesulphonic acid or naphthalenedisulphonic acid.

Other pharmaceutically compatible salts which may be mentioned are salts with customary bases, such as, for example, alkali metal salts (for example sodium or potassium salts), alkaline earth metal salts (for example calcium or magnesium salts) or ammonium salts, derived from ammonia or organic amines, such as, for example, diethylamine, triethylamine, ethyldiisopropylamine, procaine, dibenzylamine, N-methylmorpholine, dihydroabietylamine or methylpiperidine.

As used herein, the term "treat," "treating," or "treatment" herein, is meant decreasing the symptoms, markers, and/or any negative effects of a disease, disorder or condition in any appreciable degree in a patient who currently has the condition. The term "treat", "treating", or "treatment" includes alleviating symptoms of a disease, disorder, or condition e.g., alleviating the symptoms of epilepsy. In some embodiments, treatment may be administered to a subject who exhibits only early signs of the condition for the purpose of decreasing the risk of developing the disease, disorder, and/or condition.

As used herein, the term "prevent," "prevention," or "preventing" refers to any method to partially or completely prevent or delay the onset of one or more symptoms or features of a disease, disorder, and/or condition. Prevention may be administered to a subject who does not exhibit signs of a disease, disorder, and/or condition.

As used herein, "subject" means a human or animal (in the case of an animal, more typically a mammal). In one aspect, the subject is a human. In one aspect, the subject is a male. In one aspect, the subject is a female.

As used herein, the term a "fluorinated derivative" is a derivative compound that the same chemical structure as the original compound, except that at least one atom is replaced with a fluorine atom or with a group of atoms containing at least one fluorine atom.

The problem to be solved by the present invention is the identification of novel compounds for the treatment and/or prevention of epilepsy and/or other conditions ameliorated by KCNQ2/3 potassium channel opening. Although drugs for epilepsy and related disorders are available, these drugs are often not suitable for many patients for a variety of reasons. Many epilepsy drugs are associated with adverse effects. For example, many of the available epilepsy drugs are believed to significantly increase the risk of birth defects if taken during the first trimester of pregnancy. Other adverse side effects include urinary retention, neuro-psychiatric symptoms including hallucinations and psychosis, dizziness and somnolence, QT-prolonging effect, and increased risk of suicidal behavior and ideation. Some epilepsy drugs require administration of high doses due to extensive metabolism into inactive or less potent metabolites.

The present invention provides the solution of new fluorinated 2-amino-4-(benzylamino)phenylcarbamate compounds for treating epilepsy and other conditions ameliorated by KCNQ2/3 potassium channel opening. The fluorinated compounds described herein have the advantage of providing improved potency, selectivity, tissue penetration, half-life, and/or metabolic stability.

The invention also provides 18F compounds useful in methods of imaging a subject to diagnose the presence, extent, or response to therapy of a disease process. The compounds of the present invention bind with high affinity as positive allosteric modulators of neuronal potassium channels, KCNQ2/3. Imaging the distribution of F-19 compound of the present invention can be performed by either making its F-18 congener or by a displacement or blocking experiment in the effect of administering a KCNQ2/3 channel opener is seen by the resulting change in the image of a F-18 KCNQ2/3 channel opener. While the correlation of the ability of a KCNQ2/3 channel opener to bind to the positive allosteric site or the spatial distribution of KCNQ2/3 channels with a particular disease process, such as epilepsy, or propensity for that disease occurring in a patient is not currently known, having a non-invasive imaging tool may aid in determining any correlation. There are currently no known F-18 labeled KCNQ2/3 channel openers.

Compounds of the Invention

The present invention relates to novel fluorinated 2-amino-4-(benzylamino)phenylcarbamate derivatives and their use. The present invention also relates to novel 18F-containing 2-amino-4-(benzylamino)phenylcarbamate derivatives, ethyl {2-amino-6-[(benzyl)amino]pyridin-3-yl}carbamate derivatives and their use. The present invention relates the synthesis of fluorinated 2-amino-4-(benzylamino)phenylcarbamatederivatives. The present invention also relates the synthesis of 18F-containing 2-amino-4-(benzylamino)phenylcarbamate derivatives, and ethyl {2-amino-6-[(benzyl)amino]pyridin-3-yl}carbamate derivatives.

The invention provides a compound of formula A:

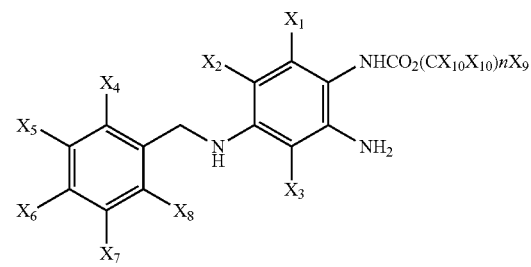

(A)

or a pharmaceutically acceptable salt or solvate thereof, wherein $X_1$, $X_2$, $X_3$, $X_4$, $X_5$, $X_6$, $X_7$, and $X_8$ are each independently selected from hydrogen, deuterium, and F;

$X_9$ and $X_{10}$ are each independently selected from hydrogen and deuterium;

n is 1, 2, or 3; provided that when $X_6$ is F, then $X_1$, $X_2$, $X_3$, $X_4$, $X_5$, $X_7$ and $X_8$ are not all hydrogen. In one aspect, the invention provides a compound of formula A, provided that the compound has at least one fluorine atom.

While all of the compounds of this invention are useful, certain classes are preferred. The following paragraphs describe certain preferred classes of a compound of formula A, wherein:

a-a) at least one of $X_1$, $X_2$, $X_3$, $X_4$, $X_5$, $X_6$, $X_7$ and $X_8$ is F;

b-a) one of $X_1$, $X_2$, $X_3$, $X_4$, $X_5$, $X_7$ and $X_8$ is F;

c-a) two of $X_1$, $X_2$, $X_3$, $X_4$, $X_5$, $X_6$, $X_7$ and $X_8$ are F;

d-a) three of $X_1$, $X_2$, $X_3$, $X_4$, $X_5$, $X_6$, $X_7$ and $X_8$ are F;

e-a) the remaining $X_1$, $X_2$, $X_3$, $X_4$, $X_5$, $X_6$, $X_7$ and/or $X_8$ are each hydrogen;

f-a) one or more of the remaining $X_1$, $X_2$, $X_3$, $X_4$, $X_5$, $X_6$, $X_7$ and/or $X_8$ are deuterium;

g-a) $X_{10}$ and $X_9$ are deuterium;

h-a) n is 1;

i-a) n is 2; and j-a) $X_{10}$ and $X_9$ are hydrogen.

The invention provides a compound of formula I:

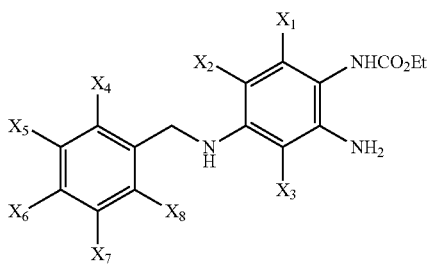

or a pharmaceutically acceptable salt or solvate thereof, wherein $X_1, X_2, X_3, X_4, X_5, X_6, X_7$ and $X_8$ are each independently selected from hydrogen, deuterium, and F, provided that when $X_6$ is F, then $X_1, X_2, X_3, X_4, X_5, X_7$ and $X_8$ are not all hydrogen. In one aspect, the invention provides a compound of formula I, provided that the compound has at least one fluorine atom.

While all of the compounds of this invention are useful, certain classes are preferred. The following paragraphs describe certain preferred classes of a compound of formula I, wherein:

a) at least one of $X_1, X_2, X_3, X_4, X_5, X_6, X_7$ and $X_8$ is F;
b) one of $X_1, X_2, X_3, X_4, X_5, X_7$ and $X_8$ is F;
c) two of $X_1, X_2, X_3, X_4, X_5, X_6, X_7$ and $X_8$ are F;
d) three of $X_1, X_2, X_3, X_4, X_5, X_6, X_7$ and $X_8$ are F;
e) the remaining $X_1, X_2, X_3, X_4, X_5, X_6, X_7$ and/or $X_8$ are each hydrogen; and
f) one or more of the remaining $X_1, X_2, X_3, X_4, X_5, X_6, X_7$ and/or $X_8$ are deuterium.

In one aspect, the invention provides a compound of formula II:

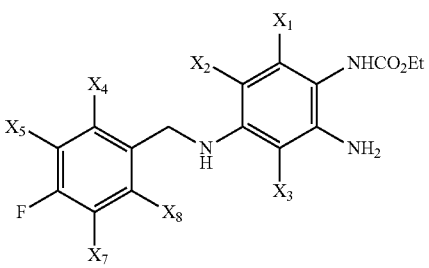

or a pharmaceutically acceptable salt or solvate thereof, wherein $X_1, X_2, X_3, X_4, X_5, X_7$ and $X_8$ are each independently selected from hydrogen, deuterium, and F, provided that $X_1, X_2, X_3, X_4, X_5, X_7$ and $X_8$ are not all hydrogen.

The following paragraphs describe certain preferred classes of a compound of formula II, wherein:

a-1) at least one of $X_1, X_2, X_3, X_4, X_5, X_7$ and $X_8$ is fluorine;
b-1) one of $X_1, X_2, X_3, X_4, X_5, X_7$ and $X_8$ is fluorine;
c-1) two of $X_1, X_2, X_3, X_4, X_5, X_7$ and $X_8$ are fluorine;
d-1) the remaining $X_1, X_2, X_3, X_4, X_5, X_7$ and/or $X_8$ are each hydrogen; and
e-1) one or more of the remaining $X_1, X_2, X_3, X_4, X_5, X_7$ and/or $X_8$ are deuterium.

In one aspect, the invention provides a compound of formula III:

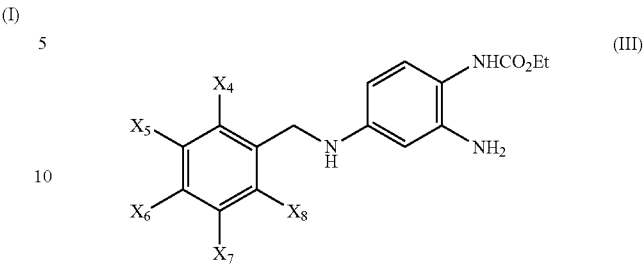

or a pharmaceutically acceptable salt or solvate thereof, wherein $X_4, X_5, X_6, X_7$ and $X_8$ are each independently selected from hydrogen, deuterium, and F, provided that when $X_6$ is F, then $X_4, X_5, X_7$ and $X_8$ are not all hydrogen.

The following paragraphs describe certain preferred classes of a compound of formula III, wherein:

a-2) at least one of $X_4, X_5, X_7$ and $X_8$ is fluorine;
b-2) one of $X_4, X_5, X_7$ and $X_8$ is fluorine;
c-2) two of $X_4, X_5, X_6, X_7$ and $X_8$ are fluorine;
d-2) $X_4$ is fluorine;
e-2) $X_5$ is fluorine;
f-2) $X_7$ is fluorine;
g-2) $X_8$ is fluorine;
h-2) the remaining $X_4, X_5, X_6, X_7$ and/or $X_8$ are each hydrogen; and
i-2) one or more of the remaining $X_4, X_5, X_6, X_7$ and/or $X_8$ are deuterium.

In one aspect, the invention provides a compound of formula IV:

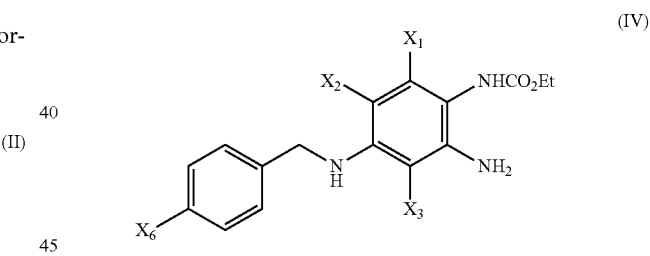

or a pharmaceutically acceptable salt or solvate thereof, wherein $X_1, X_2, X_3$, and $X_6$ are each independently selected from hydrogen, deuterium, and F, provided that when $X_6$ is F, then $X_1, X_2$, and $X_3$ are not all hydrogen. In one aspect, the invention provides a compound of formula IV, provided that the compound has at least one fluorine atom.

The following paragraphs describe certain preferred classes of a compound of formula IV, wherein:

a-3) one of $X_1, X_2$, and $X_3$ is fluorine;
b-3) one of $X_1, X_2$, and $X_3$ is fluorine;
c-3) two of $X_1, X_2$, and $X_3$ are fluorine;
d-3) $X_1$ is fluorine;
e-3) $X_2$ is fluorine;
f-3) $X_3$ is fluorine;
g-3) $X_6$ is fluorine and one of $X_1, X_2$, and $X_3$ is fluorine;
h-3) $X_6$ is hydrogen and at least one of $X_1, X_2$, and $X_3$ is fluorine;
i-3) $X_2$ and $X_3$ are fluorine;
j-3) the remaining $X_1, X_2$, and/or $X_3$ are each hydrogen; and
k-3) one or more of the remaining $X_1, X_2$, and/or $X_3$ are deuterium.

It will be understood that the above classes may be combined to form additional classes, as for example the combination of selections for two or more substituents.

For example, for formula A, class e-a) can be combined with one of classes a-a), b-a), c-a), or d-a);

For formula A, class e-a) can be combined with one of classes a-a), b-a), c-a), or d-a) and further combined with class j-a) and class h-a);

For formula A, class e-a) can be combined with one of classes a-a), b-a), c-a), or d-a) and further combined with class j-a) and class i-a);

For formula A, class f-a) can be combined with one of classes a-a), b-a), c-a), or d-a);

For formula A, class f-a) can be combined with one of classes a-a), b-a), c-a), or d-a) and further combined with class g-a) and class h-a);

For formula A, class f-a) can be combined with one of classes a-a), b-a), c-a), or d-a) and further combined with class g-a) and class i-a);

For formula I, class e) can be combined with one of classes a), b), c), or d); For formula I, class f) can be combined with one of classes a), b), c), or d);

For formula II, class d-1) can be combined with one of classes a-1), b-1), or c-1);

For formula II, class e-1) can be combined with one of classes a-1), b-1), or c-1);

For formula III, class h-2) can be combined with one of classes a-2), b-2), c-2), d-2), e-2), f-2), or g-2);

For formula III, class i-2) can be combined with one of classes a-2), b-2), c-2), d-2), e-2), f-2), or g-2);

For formula IV, class j-3) can combined with one of classes a-3), b-3), c-3), d-3), e-3), f-3), g-3), h-3), or i-3); and For formula IV, class k-3) can combined with one of classes a-3), b-3), c-3), d-3), e-3), f-3), g-3), h-3), or i-3).

In one aspect, the invention provides a compound of Table 1.

In one aspect, a compound of the invention is a pharmaceutically acceptable salt. In one aspect, a compound of the invention is a solvate. In one aspect, a compound of the invention is a hydrate.

The present invention relates to pharmaceutical compositions comprising one of the compounds of the invention as an active ingredient. In one aspect, the invention provides a pharmaceutical composition comprising at least one compound of formulae A, I, II, III, or IV or a pharmaceutically acceptable salt or solvate thereof and one or more pharmaceutically acceptable carrier or excipient. In one aspect, the invention provides a pharmaceutical composition comprising at least one compound of Table 1.

The present invention relates to a method of synthesizing a compound of the invention or a pharmaceutically acceptable salt or solvate thereof. A compound of the invention can be synthesized using a variety of methods known in the art. The schemes and description below depict general routes for the preparation of a compound of the invention. The steps described herein involving nitro group reduction, benzylalkylation, and conversion of an aromatic amine to a carbamate can be carried out in different sequences. For example, Schemes 1A and 2A depict two possible preparations.

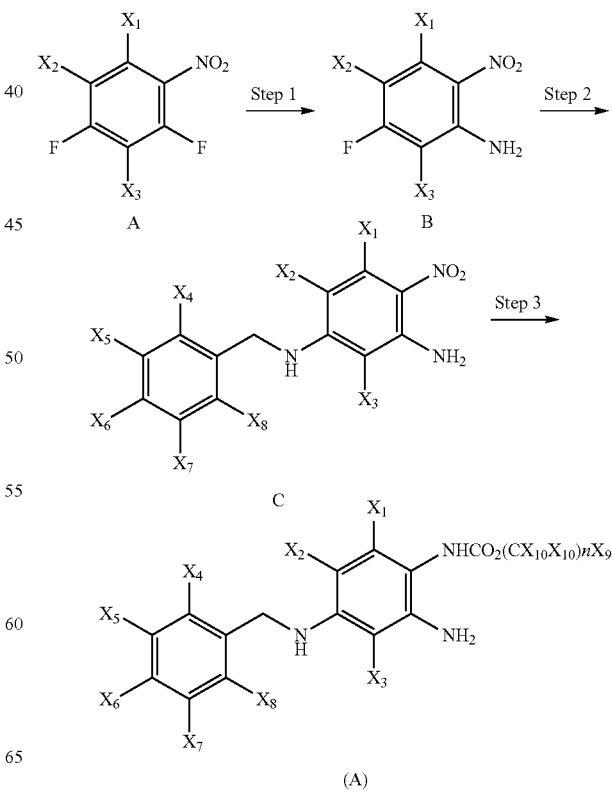

Schemes 1A and 2A outline preparations for a compound of the invention of Formula A. It is understood that Formulae I, II, III, and IV described herein are subsets of Formula A. Thus, the preparations described for a compound of Formula A can also be applied for the preparation of a compound of Formulae I, II, III, and/or IV.

The preparations outlined in Schemes 1A and 2A begin with Compounds A or E. Both of which are commercially available from chemical vendors.

In Step 1 of Scheme 1A, the fluorine atom which is adjacent to the nitro group of Compound A is converted to an amino group to form Compound B. For example, Compound A can be treated with methanolic ammonia to form Compound B. In Step 2, the remaining fluorine atom is coupled to a benzyl amino compound to form Compound C. For example, the fluorine atom of Compound B can be coupled to 4-fluorobenzylamine using $Et_3N$, $I_2$, and DMSO to form Compound C. In Step 3, the nitro group of Compound C is reduced and a carbamate is formed to provide a compound of Formula I. For example, the nitro group of Compound C can be reduced using zinc powder and ammonium chloride in methanol. Formation of the carbamate can be carried out using ethyl chloroformate. In some cases, Compounds B are commercially available in which case the synthesis scheme begins at Step 2.

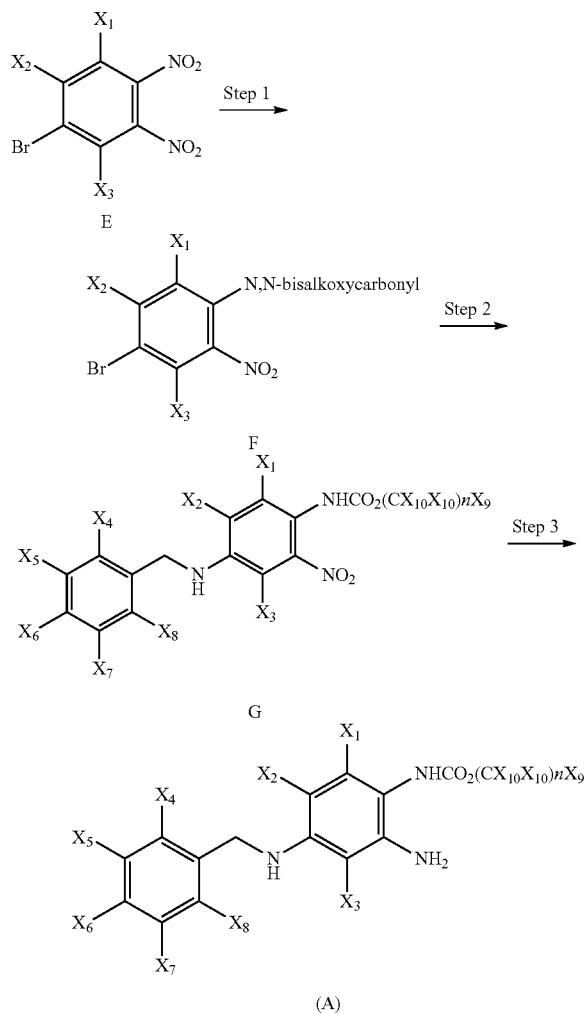

In Step 1 of Scheme 2A, the amino group of Compound E is converted to a N,N-bis-alkoxycarbonyl group to form Compound F. For example, Compound E can be treated with ethyl chloroformate to form Compound F. In Step 2, the bromine atom of Compound F is coupled to a benzyl amino compound, and the N,N-bis-alkoxycarbonyl group is converted to a carbamate to form Compound G. For example, the bromine atom of Compound F can be coupled to 4-fluorobenzylamine and the N,N-bis-alkoxycarbonyl group can be converted to an ethyl carbamate using $Cs_2CO_3$, $Pd_2(dba)_3$, and Xantphos as reagents to form Compound G. In Step 3, the nitro group is reduced to an amino group to provide a compound of Formula A. For example, the nitro group of Compound G can be reduced using zinc powder and ammonium chloride in methanol.

The present invention also comprehends deuterium labeled compounds, wherein one or more hydrogen atoms is replaced by a deuterium atom having an abundance of deuterium at that position that is substantially greater than the natural abundance of deuterium, which is 0.015%. The present invention comprehends deuterium labeled compounds where the ethyl carbamate is deuterated e.g., compound 10A described herein.

The term "deuterium enrichment factor" as used herein means the ratio between the deuterium abundance and the natural abundance of a deuterium. In one aspect, a compound of the invention has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Deuterium labeled compounds can be prepared using any of a variety of art-recognized techniques. For example, deuterium labeled compounds of formula I, II, III, IV, V, VI, VII, VIII, or IX and compounds listed in Tables 1 and 3 of this invention.

A compound of the invention or a pharmaceutically acceptable salt or solvate thereof that contains the aforementioned deuterium atom(s) is within the scope of the invention. Further, substitution with heavier deuterium, i.e., $^2H$, can afford certain therapeutic advantages resulting from greater metabolic stability, for example increased in vivo half-life or reduced dosage requirements.

In one aspect, the invention provides a deuterium labeled compound selected from Table

TABLE 2

| Compound # | Chemical Structure |
|---|---|
| 10A | ![structure with NHCO₂CD₂CD₃, NH₂, F groups] |

In one aspect, a deuterium labeled compound of the invention is a pharmaceutically acceptable salt. In one aspect, a deuterium labeled compound of the invention is a solvate. In one aspect, a deuterium labeled compound of the invention is a hydrate.

The present invention relates to pharmaceutical compositions comprising one of the deuterium labeled compounds of the invention as an active ingredient. In one aspect, the invention provides a pharmaceutical composition comprising at least one deuterium labeled compound of formula I, II, III, IV, V, VI, VII, VIII, or IX or a pharmaceutically acceptable salt or solvate thereof and one or more pharmaceutically acceptable carrier or excipient. In one aspect, the invention provides a pharmaceutical composition comprising at least one compound of Table 2.

The present invention relates to a method of synthesizing a deuterium labeled compound of the invention or a pharmaceutically acceptable salt or solvate thereof.

The deuterium labeled compounds of the invention can be prepared using any of a variety of art-recognized techniques. The deuterium labeled compounds can generally be prepared by carrying out the procedures disclosed in Schemes and the description provided herein. For example, a deuterium labeled compound can be prepared by starting with deuterium labeled Compound A or E and/or substituting a readily available deuterium labeled reagent for a non-deuterium labeled reagent.

The scheme and description below depicts a general route for the incorporation of deuterium label to produce a deuterium labeled compound of the invention.

Scheme 3A

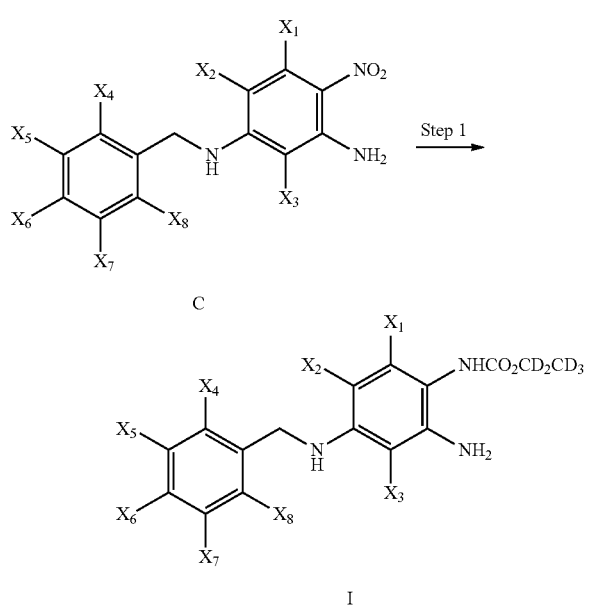

Scheme 3A outlines a preparation for a deuterium labeled compound of the invention having the structure I. The preparation begins with Compound C (from Scheme 1A described herein). In Step 1, the nitro group of Compound C is reduced and then the deuterium label is introduced via formation of a carbamate. For example, the nitro group of Compound C can be reduced using zinc powder and ammonium chloride in methanol and the carbamate can be formed using ethyl-d5 chloroformate to provide Compound I.

The present invention also relates to 18F compounds useful for positron emission tomography (PET) imaging of the distribution of a compound of the invention by the imaging of the distribution of the 18F isotopic analog of the compound, or the functional status of KCNQ2/3 voltage-gated potassium channels in a subject. Imaging the KCNQ2/3 voltage-gated potassium channels provides information to diagnose diseases associated with deficiencies in the function of the channels such as epilepsy, monitor therapy by compounds of the invention, of other compounds that result in KCNQ2/3 opening.

The invention provides an 18F compound of formula V:

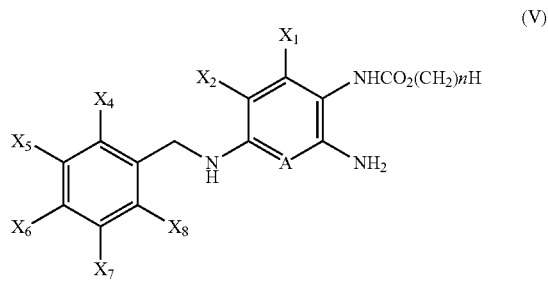

or a pharmaceutically acceptable salt thereof, wherein A is N or C—$X_3$; $X_1$, $X_2$, $X_3$, $X_4$, $X_5$, $X_6$, $X_7$, and $X_8$ are each independently selected from hydrogen, 19F and 18F; n is 2 or 3, provided that one of $X_1$, $X_2$, $X_3$, $X_4$, $X_5$, $X_6$, $X_7$, and $X_8$ is 18F.

While all of the 18F compounds of this invention are useful, certain classes are preferred. The following paragraphs describe certain preferred classes of a compound of formula V, wherein:

a-4) at least one of $X_1$, $X_2$, $X_3$, $X_4$, $X_5$, $X_6$, $X_7$, and $X_8$ is 19F;
b-4) one of $X_1$, $X_2$, $X_3$, $X_4$, $X_5$, $X_6$, $X_7$, and $X_8$ is 19F;
c-4) two of $X_1$, $X_2$, $X_3$, $X_4$, $X_5$, $X_6$, $X_7$, and $X_8$ are 19F;
d-4) A is N;
e-4) A is C—$X_3$ and $X_3$ is hydrogen;
f-4) A is C—$X_3$ and $X_3$ is 19F;
g-4) $X_6$ is 18F;
h-4) $X_1$ is 18F;
i-4) $X_6$ is 19F; and
j-4) the remaining $X_1$, $X_2$, $X_3$, $X_4$, $X_5$, $X_7$, and/or $X_8$ are each hydrogen.

In one aspect, the invention provides an 18F compound of formula VI:

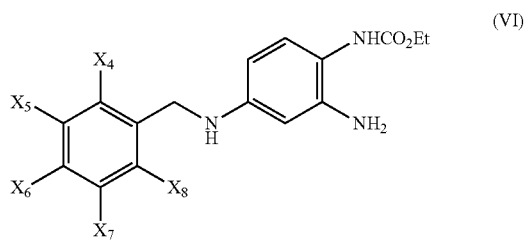

or a pharmaceutically acceptable salt thereof, wherein $X_4$, $X_5$, $X_6$, $X_7$ and $X_8$ are each independently selected from hydrogen, 19F, and 18F, provided that one of $X_4$, $X_5$, $X_6$, $X_7$ and $X_8$ is 18F.

The following paragraphs describe certain preferred classes of a compound of formula VI, wherein:

a-5) at least one of $X_4$, $X_5$, $X_6$, $X_7$ and $X_8$ is 19F;
b-5) one of $X_4$, $X_5$, $X_6$, $X_7$ and $X_8$ is 19F;
c-5) one of $X_4$, $X_5$, $X_6$, $X_7$ and $X_8$ is 18F;
d-5) $X_4$ is 18F;
e-5) $X_5$ is 18F;

f-5) $X_6$ is 18F;
g-5) $X_7$ is 18F;
h-5) $X_8$ is 18F;
i-5) $X_6$ is 18F or 19F;
j-5) $X_6$ is 19F; and
k-5) the remaining $X_4$, $X_5$, $X_6$, $X_7$, and/or $X_8$ are each hydrogen.

In one aspect, the invention provides an 18F compound of formula VII:

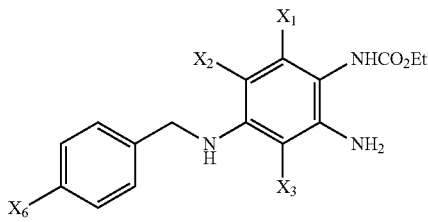

(VII)

or a pharmaceutically acceptable salt thereof, wherein $X_1$, $X_2$, $X_3$, and $X_6$ are each independently selected from hydrogen, 18F, and 19F, provided that one of $X_1$, $X_2$, $X_3$, and $X_6$ is 18F.

The following paragraphs describe certain preferred classes of a compound of formula VII, wherein:
a-6) at least one of $X_1$, $X_2$, $X_3$, and $X_6$ is 19F;
b-6) one of $X_1$, $X_2$, $X_3$, and $X_6$ is 19F;
c-6) two of $X_1$, $X_2$, $X_3$, and $X_6$ are 19F;
d-6) $X_6$ is 18F and $X_1$, $X_2$, and $X_3$ are each independently selected from hydrogen and 19F, provided that least one of $X_1$, $X_2$, $X_3$ is 19F;
e-6) $X_6$ is 18F and $X_1$ is 19F;
f-6) $X_6$ is 18F and $X_2$ is 19F;
g-6) $X_6$ is 18F and $X_3$ is 19F;
h-6) $X_6$ is H and one of $X_1$, $X_2$, and $X_3$ is 18F;
i-6) $X_6$ is H and $X_1$ is 18F;
j-6) $X_6$ is H and $X_2$ is 18F;
k-6) $X_6$ is H and $X_3$ is 18F;
l-6) $X_1$ is 18F or 19F;
m-6) $X_2$ is 18F or 19F;
n-6) $X_3$ is 18F or 19F;
o-6) $X_6$ is 18F or 19F;
p-6) $X_6$ is 19F and $X_1$ is 18F;
q-6) $X_6$ is 19F and $X_2$ is 18F;
r-6) $X_6$ is 19F and $X_3$ is 18F;
s-6) at least one of $X_1$, $X_2$, and $X_3$ is 19F; and
t-6) the remaining $X_1$, $X_2$, $X_3$, and/or $X_6$ are each hydrogen.

In one aspect, the invention provides an 18F compound of formula (VIII):

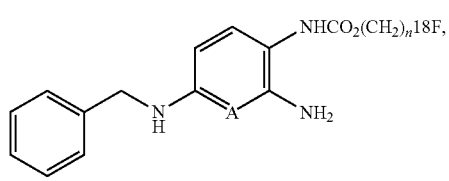

(VIII)

or a pharmaceutically acceptable salt thereof, wherein n is 2 or 3, A is N or C—$X_3$, and $X_3$ is selected from hydrogen or 19F.

The following paragraphs describe certain preferred classes of a compound of formula VIII, wherein:
a-7) A is N;
b-7) A is C—$X_3$ and $X_3$ is hydrogen;
c-7) A is C—$X_3$ and $X_3$ is 19F;
d-7) n is 2; and
e-7) n is 3.

In one aspect, the invention provides an 18F compound of formula (IX):

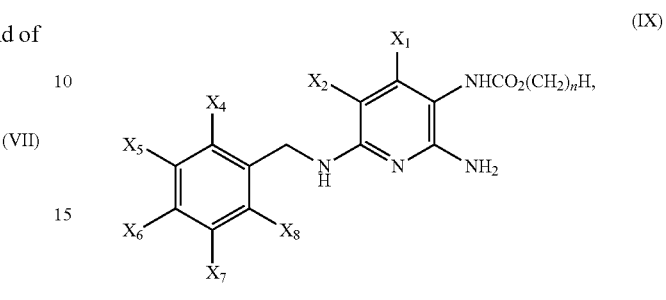

(IX)

or a pharmaceutically acceptable salt thereof, wherein $X_1$, $X_2$, $X_4$, $X_5$, $X_6$, $X_7$, and $X_8$ are each independently selected from hydrogen 19F and 18F; n is 2 or 3, provided that one of $X_1$, $X_2$, $X_4$, $X_5$, $X_6$, $X_7$, and $X_8$ is 18F.

The following paragraphs describe certain preferred classes of a compound of formula IX, wherein:
a-8) at least one of $X_1$, $X_2$, $X_4$, $X_5$, $X_6$, $X_7$, and $X_8$ is 19F;
b-8) one of $X_1$, $X_2$, $X_4$, $X_5$, $X_6$, $X_7$, and $X_8$ is 19F;
c-8) two of $X_1$, $X_2$, $X_4$, $X_5$, $X_6$, $X_7$, and $X_8$ are 19F;
d-8) $X_1$ is 18F or 19F;
e-8) $X_2$ is 18F or 19F;
f-8) $X_6$ is 18F or 19F;
g-8) $X_6$ is 18F and $X_1$ is 19F;
h-8) $X_6$ is 19F and $X_1$ is 18F;
i-8) $X_6$ is 18F and $X_2$ is 19F;
j-8) $X_6$ is 19F and $X_2$ is 18F; and
k-8) the remaining $X_1$, $X_2$, $X_4$, $X_5$, $X_6$, $X_7$, and $X_8$ are each hydrogen.

It will be understood that the above classes may be combined to form additional classes, as for example the combination of selections for two or more substituents. For example, For formula V, class j-4) can be combined with one of classes a-4), b-4), c-4), g-4), h-4, or i-4);

For formula V, class j-4) can be combined with one of classes a-4), b-4), c-4), g-4), h-4, or i-4), which can be further combined with class d-4), e-4), or f-4);

For formula VI, class k-5) can be combined with one of classes a-5), b-5), c-5), d-5), e-5), f-5), g-5), h-5), i-5), and j-5);

For formula VII, class t-6) can be combined with one of classes a-6), b-6), c-6), e-6), f-6), g-6), h-6), i-6), j-6), k-6), l-6), n-6), o-6), p-6), q-6), r-6), and s-6);

For formula VIII, one of classes a-7), b-7), or c-7) can be combined with one of classes d-7) or e-7);

For formula IX, class k-8) can be combined with one of classes a-8), b-8), c-8), d-8), e-8), f-8), g-8), h-8), i-8), and j-8).

In one aspect the invention provide an 18F compound selected from Table 3.

TABLE 3

| Compound # | Chemical Structure |
|---|---|
| 5A | 4-($^{18}$F)-benzyl group attached via NH to a benzene ring bearing NHCO$_2$Et and NH$_2$ substituents |
| 6A | 4-F-benzyl group attached via NH to a benzene ring bearing NHCO$_2$Et, NH$_2$, and $^{18}$F substituents |
| 7A | 4-($^{18}$F)-benzyl group attached via NH to a pyridine ring bearing NHCO$_2$Et and NH$_2$ substituents |
| 8A | 4-F-benzyl group attached via NH to a pyridine ring bearing $^{18}$F, NH-C(O)-OEt, and NH$_2$ substituents |
| 9A | 4-($^{18}$F)-benzyl group attached via NH to a benzene ring bearing NHCO$_2$Et, NH$_2$, and F substituents |

In one aspect, an 18F compound of the invention is a pharmaceutically acceptable salt.

The present invention relates to pharmaceutical compositions comprising one of the 18F compounds of the invention suitable for parenteral injection. In one aspect, the invention provides a pharmaceutical composition comprising at least one 18F compound of formulae V, VI, VII, VIII or IX or a pharmaceutically acceptable salt thereof and one or more pharmaceutically acceptable carrier or excipient. In one aspect, the invention provides a pharmaceutical composition comprising at least one 18F compound of Table 2.

Methods of Synthesizing 18F Compounds 18F compounds of the invention may be synthesized by reacting a precursor compound with F-18 fluoride via an $S_N2$ displacement of an appropriate leaving group on the precursor compound. Examples of such leaving groups include sulfonic acid esters such as toluenesulfonate (tosylate), methanesulfonate (mesylate), or trifluoromethanesulfonate (triflate). The leaving group may also be a halide, a nitro group, a trimethylammonium group, a phosphine oxide (via Mitsunobu reaction), or an internal leaving group (such as an epoxide or cyclic sulfate). In some embodiments, 18F compounds of the invention can be synthesized from highly activated, dry, K18F, which is made more reactive by the addition of potassium sequestering cryptands such as 18-crown-6 or kryptofix [2.2.2].

For some compounds containing aromatic or heterocyclic ring structures that are not amenable to nucleophilic substitution by activated fluoride, an electrophilic fluorination method may be used. These methods include reaction with F-18 fluorine gas (F2) or F-18 N-chloromethyl-N-fluorotriethylenediammonium bis(tetrafluoroborate) (F-18-TEDA). Other methods of electrophilic fluorination include the use of the palladium(IV) complex described in Science, 2011, 334, pp. 639-642; or the diaryliodonium salts described in Organic & Biomolecular Chemistry, 2011, 9, pp. 8346-8355.

The foregoing chemical transformations may be conducted using techniques which would be readily apparent to one of ordinary skill in the art, in combination with the teachings described herein. In some cases, methods of synthesizing the F-18 compounds of the invention may include the use of one or more reaction solvents. Representative reaction solvents include, for example, acetonitrile, acetone, DMF, DMSO, THF, ethylacetate, toluene, dichloromethane and chloroform. The acidity or basicity of the reaction solution may be controlled by the use of one or more organic acids or bases, for example, triethylamine or diisopropylethylamine, or trifluoroacetic acid. In some cases the chemical transformations may be carried out at ambient temperatures or under elevated temperatures and may be protected from oxygen and water by nitrogen, argon or helium atmosphere.

In some embodiments, temporary protecting groups may be used to prevent other reactive functionality, such as amines, thiols, alcohols, phenols, and carboxylic acids, from participating or interfering in the fluorination reaction. Representative amine protecting groups include, for example, tert-butoxycarbonyl and trityl (removed under acid conditions), Fmoc (removed by the use of secondary amines such as piperidine), and benzyloxycarbonyl (removed by strong acid or by catalytic hydrogenolysis). The trityl group may also be used for the protection of thiols, phenols, and alcohols. In certain embodiments the carboxylic acid protecting groups include, for example, tert-butyl ester (removed by mild acid), benzyl ester (usually removed by catalytic hydrogenolysis), and alkyl esters such as methyl or ethyl (usually removed by mild base). All protecting groups may be removed at the conclusion of the synthesis using the conditions described above for the individual protecting groups, and the final product may be purified by techniques which would be readily apparent to one of ordinary skill in the art, in combination with the teachings described herein.

The present invention relates to a method of synthesizing an 18F compound of the invention or a pharmaceutically acceptable salt thereof. There are several methods for synthesizing F-18 compounds of the present invention that are comprised of F-18 substituents on aromatic rings: nucleophilic displacement of a leaving group such as bromo, nitro, or trimethylamino by strongly nucleophilic F-18 fluoride ion (Scheme 3A); palladium-assisted electrophilic aromatic substitution (Schemes 4A, 4B, and 4C); and nickel-assisted aromatic fluorination Scheme 5A). In each of these reaction schemes the aromatic ring that is to be substituted by F-18 is shown bearing a substituent -R, wherein R represents the remainder of the desired molecule of the present invention.

Scheme 3A: Nucleophilic substitution:

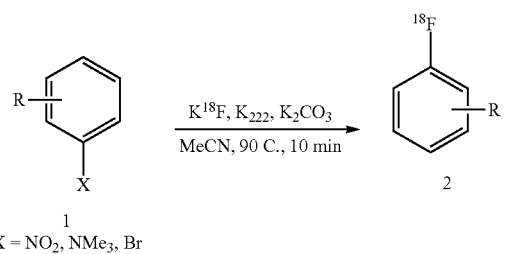

X = NO$_2$, NMe$_3$, Br

The process described above in Scheme 3A involves acquiring 18F-fluoride as an aqueous solution, available from a number of commercial radiopharmacies, potassium carbonate and Kryptofix[2.2.2] added and the water evaporated to yield a dry residue. A solution of the Compound 1 dissolved in acetonitrile is added and the mixture is heated under nitrogen at elevated temperature for the time necessary to complete the reaction. Alternatives solvents to acetonitrile such as dimethylsulfoxide can be used to allow higher heating temperatures, e.g. up to 130 C.

Schemes 4A, 4B, and 4C: Palladium-Assisted Electrophilic Aromatic Substitution

The process involves making a palladium(II)-aryl complex with the aryl group attached to the palladium atom at the point of substitution with 18F desired using standard organometallic chemistry reaction conditions. Particularly effective is to make a alkylboronate-substituted aryl group and to react that with the palladium(II) acetate complex shown in Scheme 4A in an organic solvent.

Scheme 4A

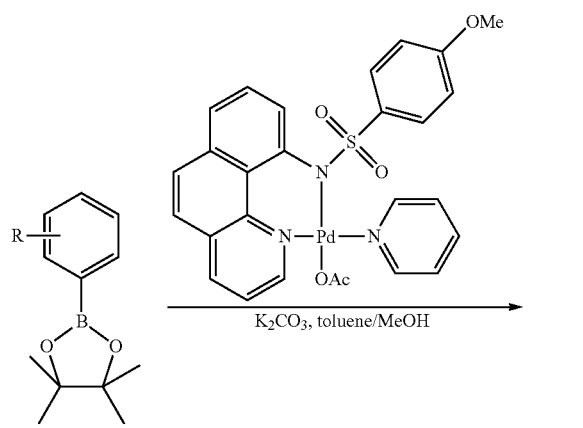

A 18F-Palladium(IV)-Fluoride Complex is then Made as Shown in Scheme 4B.

Scheme 4B

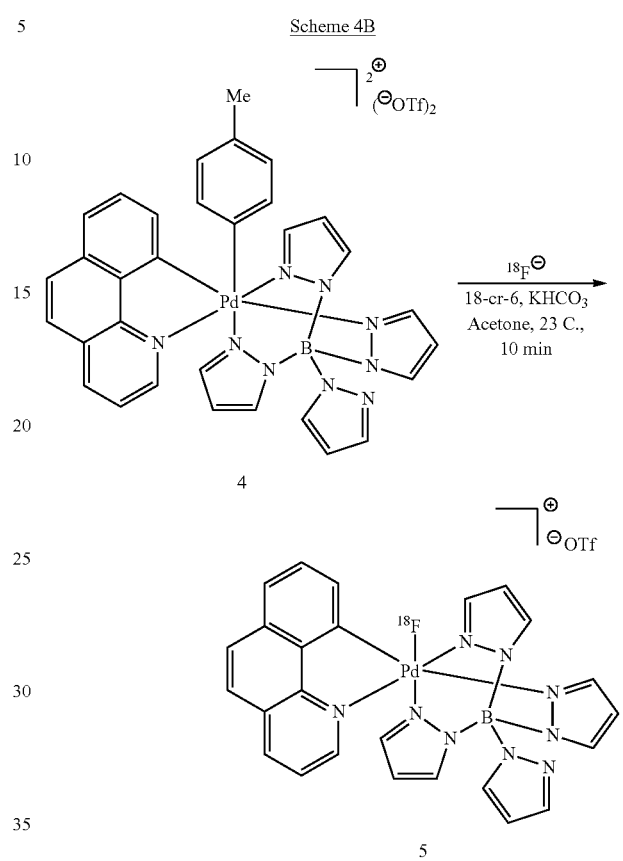

18F-Fluoride as an aqueous solution, available from a number of commercial radiopharmacies, potassium bicarbonate and 18-crown-6 are combined and the water evaporated to yield a dry residue. A solution of the compound 4 dissolved in acetone is added to form compound 5, the 18F-palladium(IV)-fluoride complex.

The 18F-palladium(IV)-fluoride complex is then reacted with palladium(II)-aryl complex made in Scheme 4A in acetone at elevated temperature for the period of time necessary to complete the reaction. This reaction is shown in Scheme 4C.

Scheme 4C

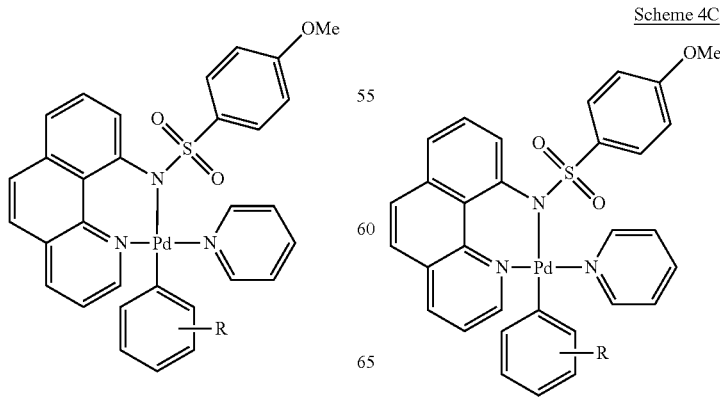

19
-continued

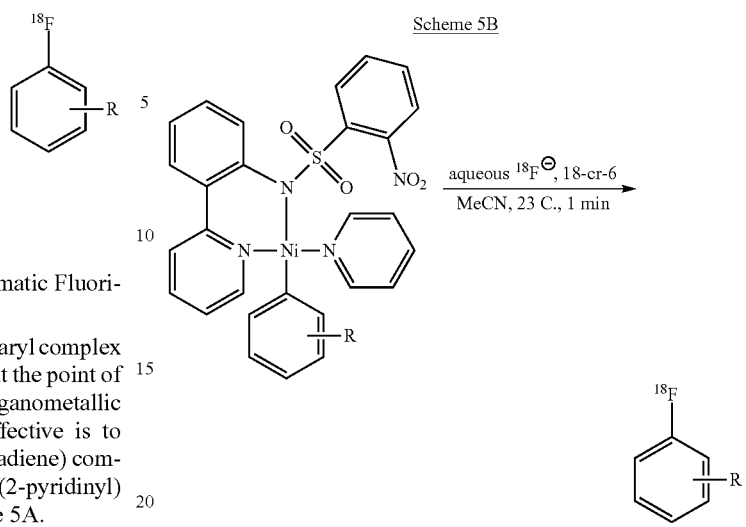

Schemes 5A, 5B, and 5C: Nickel-Assisted Aromatic Fluorination

This process involve synthesizing a nickel(II) aryl complex with the aryl group attached to the nickel atom at the point of substitution with 18F desired using standard organometallic chemistry reaction conditions. Particularly effective is to react an arylbromide with the nickel(0)cyclooctadiene) complex, Ni(COD)$_2$ followed by reacting with the 2-(2-pyridinyl) anilinosulfonamide silver salt shown in Scheme 5A.

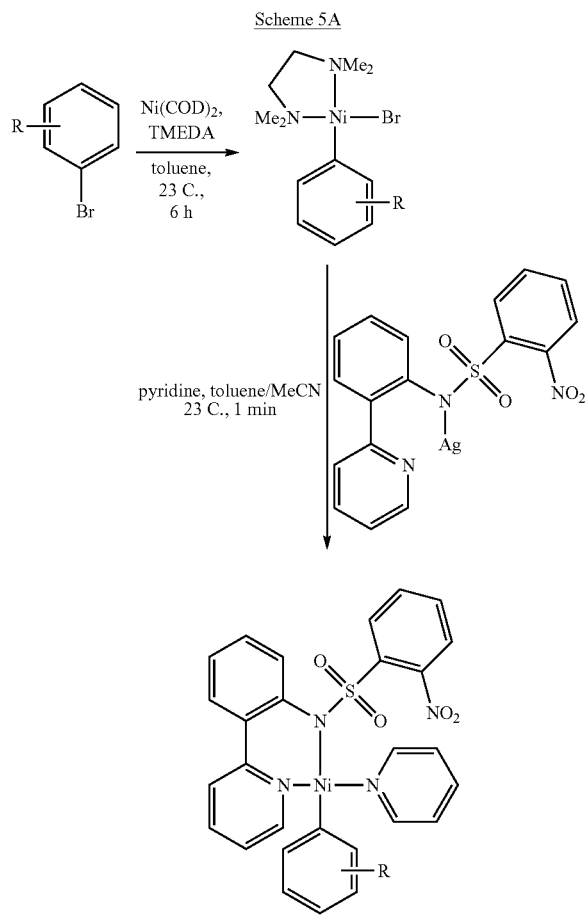

The nickel(II)-aryl complex is then combined simultaneously with a commercially available hypervalent iodine oxidant and 18F-fluoride as a dilute aqueous solution in acetonitrile containing 18-crown-6. This process step is shown in Scheme 5B. The desires 18F-aryl compound is made nearly instantaneously at room temperature.

Methods of Use

The present invention relates to methods for the use of compounds of the invention. The compounds of the invention have a useful pharmacological activity spectrum and are therefore particularly suitable for the prophylaxis and/or treatment of diseases or disorders.

The present invention provides the use of a compound of the invention for the preparation of a medicament for administration to a subject for use in the treatment or prevention of disorders.

In one aspect, the invention provides the use of a compound of the invention in the preparation of a medicament for administration to a subject for use in the treatment or prevention of conditions ameliorated by KCNQ2/3 potassium channel opening. In one aspect, the invention provides a method treating a subject suffering from or susceptible to conditions ameliorated by KCNQ2/3 potassium channel opening, comprising administering to the subject in need thereof an effective amount of a compound of the invention or a pharmaceutically acceptable salt or solvate thereof.

In one aspect, the invention provides a method of treating or preventing epilepsy in a subject in need thereof comprising administering to the subject an effective amount of a compound of the invention or a pharmaceutically acceptable salt or solvate thereof.

In one aspect, the invention provides a method of producing an anti-epileptic, muscle relaxing, fever reducing, peripherally analagesic or anti-convulsive effect in a subject in need thereof comprising administering to the subject an effective amount of a compound of the invention or a pharmaceutically acceptable salt or solvate thereof.

In one aspect, the invention provides compounds that are useful as an anti-convulsant. They are therefore useful in treating epilepsy. In one aspect, the invention provides a method of treating a subject suffering from or susceptible to epilepsy comprising administering to the subject in need thereof an effective amount of a compound of the invention or a pharmaceutically acceptable salt or solvate thereof. Compound of the invention may be used to improve the condition of a host, typically a human being, suffering from epilepsy. They may be employed to alleviate the symptoms of epilepsy in a host. "Epilepsy" is intended to include the following seizures:—simple partial seizures, complex partial seizures, secondary generalized seizures, generalized seizures including absence seizures, myoclonic seizures, clonic seizures, tonic seizures, tonic clonic seizures and atonic seizures.

Partial-onset seizures are the most common type of seizure in adult patients. For partial seizures, there is a focal epileptic zone (site of seizure onset), and seizure activity is initially limited to one hemisphere. Partial seizures can be further sub-divided into simple partial (without impairment of consciousness), complex partial (with impairment of consciousness with or following a simple partial onset) and secondarily generalized (i.e., partial seizures, either simple or complex, which evolve to generalized tonic-clonic seizures). Simple partial seizures, depending on the anatomical site of origin of the seizure, may have motor, somatosensory or special sensory, autonomic or psychic signs or symptoms. In one aspect, the invention provides a method for the adjunctive treatment of adults with partial-onset seizures comprising administering to the subject an effective amount of a compound of the invention or a pharmaceutically acceptable salt thereof.

In one aspect, the invention provides a method for the treating a subject suffering from or susceptible to epilepsy comprising administering to the subject in need thereof an effective amount of a combination of a compound of the invention and one or more anti-epileptic drugs (AEDs). There are different types of AEDs. For example, narrow-spectrum AEDs include e.g., phenyloin (Dilantin), phenobarbital, carbamazepine (Tegretol), oxcarbazepine (Trileptal), gabapentin (Neurontin), pregabalin (Lyrica), lacosamide (Vimpat), and vigabatrin (Sabril). Broad spectrum AEDs include e.g., valproic acid (Depakote), lamotrigine (Lamictal), topiramate (Topamax), zonisamide (Zonegran), levetiracetam (Keppra), clonazepam (Klonopin), and rufinamide (Banzel). In one aspect, the AED is any AED. In one aspect, the AED is a narrow spectrum AED. In one aspect, the AED is a broad spectrum AED.

In one aspect, the invention provides a method of treating or preventing a neurotransmission disorder, CNS disorder, functional bowel disorder, neurodegenerative disease, or tinnitus in a subject in need thereof comprising administering to the subject an effective amount of a compound of the invention or a pharmaceutically acceptable salt or solvate thereof.

In one aspect, the invention provides a method of treating or preventing a cognitive disorder or migraine in a subject in need thereof comprising administering to the subject an effective amount of a compound of the invention or a pharmaceutically acceptable salt or solvate thereof.

In one aspect, the invention provides a method of treating or preventing migraine, bipolar disorder, unipolar depression, functional bowel disorders, or tinnitus in a subject in need thereof comprising administering to the subject an effective amount of a compound of the invention or a pharmaceutically acceptable salt or solvate thereof.

In one aspect, the invention provides compounds that are useful in the treatment of CNS disorders such as bipolar disorder, alternatively known as manic depression. Type I or II bipolar disorder may be treated. The compounds may thus be used to improve the condition of a human patient suffering from bipolar disorder. They may be used to alleviate the symptoms of bipolar disorder in a host. The compounds may also be used in the treatment of unipolar depression, ataxia, myokimia and anxiety.

In one aspect, the invention provides compounds that are useful in the treatment of functional bowel disorders which include non-ulcer dyspepsia, non-cardiac chest pain and in particular irritable bowel syndrome. Irritable bowel syndrome is a gastrointestinal disorder characterized by the presence of abdominal pain and altered bowel habits without any evidence of organic disease. The compounds may thus be used to alleviate pain associated with irritable bowel syndrome. The condition of a human patient suffering from irritable bowel syndrome may thus be improved.

In one aspect, the invention provides compounds that are useful as analgesics. They are therefore useful in treating or preventing pain. They may be used to improve the condition of a host, typically a human being, suffering from pain. They may be employed to alleviate pain in a host. Thus, the compounds may be used as a pre-emptive analgesic to treat acute pain such as musculoskeletal pain, post-operative pain and surgical pain, chronic pain such as chronic inflammatory pain (e.g. rheumatoid arthritis and osteoarthritis), neuropathic pain (e.g. post herpetic neuralgia, trigeminal neuralgia and sympathetically maintained pain) and pain associated with cancer and fibromyalgia. The compounds may also be used in the treatment or prevention of pain associated with migraine. The compounds may also be used in the treatment of the pain (both chronic and acute), fever and inflammation of conditions such as rheumatic fever; symptoms associated with influenza or other viral infections, such as the common cold; lower back and neck pain; headache; toothache; sprains and strains; myositis; neuralgia; synovitis; arthritis, including rheumatoid arthritis; degenerative joint diseases, including osteoarthritis; gout and ankylosing spondylitis; tendinitis; bursitis; skin related conditions, such as psoriasis, eczema, burns and dermatitis; injuries, such as sports injuries and those arising from surgical and dental procedures.

In one aspect, the invention provides a method of producing an analgesic effect in a subject in need thereof comprising administering to the subject an effective amount of a compound of the invention or a pharmaceutically acceptable salt or solvate thereof. In one aspect, the analgesic effect is a neuroprotective effect. In one aspect, the analgesic effect is a centrally acting analgesic effect.

In one aspect, the invention provides compounds that are useful in the treatment of neurodegenerative diseases, such as Alzheimer's disease, ALS, motor neuron disease, Parkinson's disease, macular degeneration and glaucoma. The compounds of the invention may also be useful in neuroprotection and in the treatment of neurodegeneration following stroke, cardiac arrest, pulmonary bypass, traumatic brain injury, spinal cord injury or the like. In one aspect, compounds of the invention are further useful in the treatment of tinnitus.

In one aspect, the invention provides compounds that are useful in the treatment of migraine.

In one aspect, the invention provides a method of preventing or reducing dependence on, or preventing or reducing tolerance, or reverse tolerance, to a dependence-inducing agent in a subject in need thereof comprising administering to the subject an effective amount of a compound of the invention or a pharmaceutically acceptable salt or solvate thereof. Examples of dependence inducing agents include opioids (e.g. morphine), CNS depressants (e.g. ethanol), psychostimulants (e.g. cocaine) and nicotine.

In one aspect, the invention provides a method of treating or preventing cancer, inflammatory disease, or ophthalmic disease in a subject in need thereof comprising administering to the subject an effective amount of a compound of the invention or a pharmaceutically acceptable salt or solvate thereof.

In one aspect, the invention provides compounds that inhibit cellular and neoplastic transformation and metastatic tumor growth and hence are useful in the treatment of certain cancerous diseases, such as colonic cancer.

In one aspect, the invention provides compounds that inhibit inflammatory processes and therefore are of use in the treatment of asthma, allergic rhinitis and respiratory distress syndrome; gastrointestinal conditions such as inflammatory bowel disease, Chron's disease, gastritis, irritable bowel syndrome and ulcerative colitis; and the inflammation in such diseases as vascular disease, migraine, periarteritis nodosa, thyroiditis, aplastic anemia, Hodgkin's disease, sclerodoma, type I diabetes, myasthenia gravis, multiple sclerosis, sorcoidosis, nephrotic syndrome, Bechet's syndrome, polymyositis, gingivitis, conjunctivitis and myocardial ischemia.

In one aspect, the invention provides compounds that are useful in the treatment of ophthalmic diseases such as retinitis, retinopathies, uveitis and of acute injury to the eye tissue.

In one aspect, the invention provides compounds that are useful for the treatment of cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Loss; and learning deficiencies.

In one aspect, the invention provides a method of producing an anxiolytic effect in a subject in need thereof comprising administering to the subject an effective amount of a compound of the invention or a pharmaceutically acceptable salt or solvate thereof. In one aspect, the invention provides a method for the treatment of anxiety and its related psychological and physical symptoms. Anxiolytics have been shown to be useful in the treatment of anxiety disorders.

In one aspect, the invention provides compounds for treatment. In one aspect, the invention provides compounds for prophylaxis. In one aspect, the invention provides compound for alleviation of established symptoms.

In one aspect, the invention provides pharmaceutical formulations that contain between about 10 to about 100, about 30 to about 60 mg of the active component(s) of the invention.

Administration may for example be in the form of tablets, capsules, pills, coated tablets, suppositories, ointments, gels, creams, powders, dusting powders, aerosols or in liquid form. Liquid application forms that may for example be considered are: oils or alcoholic or aqueous solutions as well as suspensions and emulsions. In one aspect, the invention provides forms of application that are tablets that contain between 30 and 60 mg or solutions that contain between 0.1 to 5 percent by weight of active substance.

In one aspect, a single dose of the active components of the invention can for example lie a) in the case of oral medicinal forms between about 20 and about 80 mg, about 30 to about 60 mg; b) in the case of parenteral medicinal forms (for example intravenous, intramuscular) between about 5 to about 20 mg, about 8 to about 16 mg. (The doses are in each case related to the free base)

In one aspect, it is for example possible to recommend 3 times daily 1 to 3 tablets containing about 30 to about 60 mg of active substance or for example in the case of intravenous injection 1 to 3 times daily one ampoule of about 3 to about 5 ml content with about 8 to about 16 mg substance. In the case of oral administration, the minimum daily dose is for example about 90 mg; the maximum daily dose in oral administration should not exceed about 270 mg.

For the treatment of dogs and cats, the oral individual dose is generally between about 2 and about 20 mg/kg body weight; the parenteral dose about between about 1 and about 5 mg/kg body weight.

In one aspect, a compound of the invention is used in human medicine. In one aspect, the compound of the invention is used in veterinary medicine. In one aspect, a compound of the invention is used in agriculture. In one aspect, a compound of the invention is used alone or mixed with other pharmacologically active substances.

In one aspect, the invention provides a medical device containing a compound of the invention or a pharmaceutically acceptable salt or solvate thereof.

Methods of Imaging

The 18F compounds of the invention may be used in methods of imaging a subject to diagnose the presence, extent or response to therapy of a disease process. For example, the method of imaging may comprise administering the 18F compound of the invention to the subject by intravenous injection as a bolus or an infusion, or any other method known to be appropriate for imaging a subject, and imaging the area of the subject wherein the process of imaging interest is located.

The useful dosage to be administered and the particular mode of administration will vary depending on factors such as age, weight, and particular region of the body to be imaged, as well as the diagnostic use contemplated. Typically, dosage is administered at lower levels and increased until a desirable diagnostic effect (e.g. production of an image) is achieved. In some embodiments, the 18F compounds may be administered by intravenous injection, usually in saline solution, at a dose of about 0.1 to about 100 mCi per 70 kg body weight (and all combinations and subcombinations of dosage ranges and specific dosages therein), or, in some embodiments, at a dose of about 0.5 mCi to about 50 mCi per subject. Imaging is performed using techniques well known to those of ordinary skill in the art.

The 18F compounds of the invention may be formulated for parenteral administration. These formulations must be sterile and non-pyrogenic and optionally may be comprised of one or more pharmaceutically compatible solvent, buffer, neutralization aid, stabilization aid, and solubilization aid.

Some non-limiting examples of buffers useful combination with the 18F compounds include phosphate, citrate, sulfosalicylate, and acetate. A more complete list can be found in the United States Pharmacopoeia.

Some non-limiting examples of stabilization aids include ethanol, ascorbic acid, cysteine, monothioglycerol, sodium bisufite, sodium metabisulfite, gentisic acid, and inositol.

Some non-limiting examples of solubilization aids include ethanol, glycerin, polyethyleneglycol, propylene glycol, polyoxyethylene sorbitan monooleate, sorbitan monooleate, polysorbates, poly(oxyethylene)-poly(oxypropylene)-poly (oxy ethylene) block co-polymers, and lecithin.

In one aspect, the invention provides 18F compounds for PET imaging.

In one aspect, the invention provides a method of imaging the biodistribution of an 18F compound of the invention comprising administering to a subject an effective amount of a the compound or a pharmaceutically acceptable salt thereof and imaging the subject using positron emission tomography.

In one aspect, the invention provides a method of imaging the functional status of the KCNQ2/3 potassium channel in a subject comprising administering to a subject in need thereof an effective amount of an 18F compound of the invention or a pharmaceutically acceptable salt thereof and imaging the subject using positron emission tomography.

In one aspect, the invention provides a method of imaging a neurotransmission disorder, CNS disorder, cognitive disorder, or neurodegenerative disease in a subject in need thereof comprising administering to the subject an effective amount of an 18F compound of the invention or a pharmaceutically acceptable salt thereof and imaging the subject using positron emission tomography.

In one aspect, an 18F compound of the invention is administered to a human subject.

The following Examples are illustrative and should not be interpreted in any way so as to limit the scope of the invention.

EXAMPLES

Example 1

Experimental Procedures and Compound Characterization

Example 1A

Synthesis of ethyl (2-amino-3-fluoro-4-((4-fluorobenzyl)amino)phenyl)carbamate (Compound 1A in Table 1)

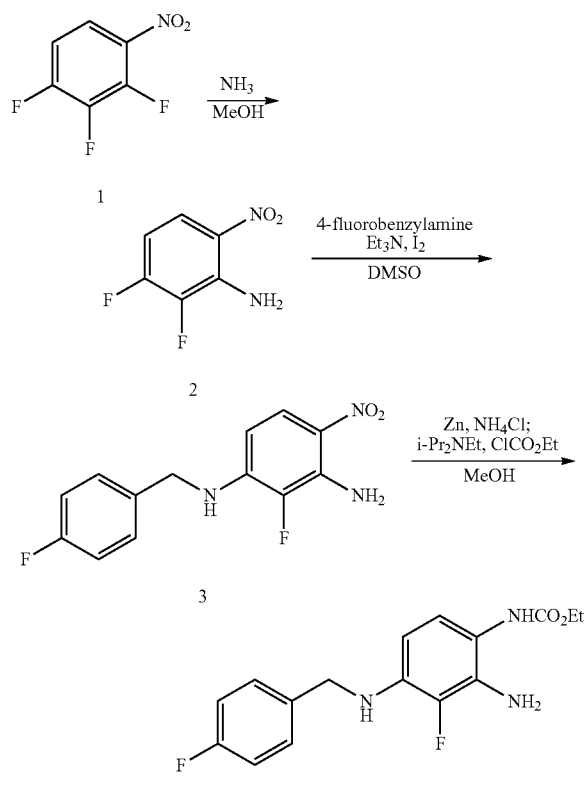

2,3-Difluoro-6-nitroaniline (2)

A solution of 1,2,3-trifluoro-4-nitrobenzene (1) (1.00 g, 5.64 mmol, 1.00 equiv) in methanolic ammonia (1.5 mL) was taken in microwave vial and heated to 70° C. for 90 min in the microwave. The solvent was evaporated under vacuum to give crude; which was purified by silica gel column chromatography (EtOAc/Hexane 1:49) to furnish compound 2 (0.350 g, 35.6%) as yellow solid. TLC: 10% EtOAc/Hexane ($R_f$: 0.10); $^1$H NMR (500 MHz, DMSO-$d_6$): δ 7.94-7.91 (m, 1H), 7.51 (s, 2H), 6.75-6.70 (m, 1H); LC-MS: m/z=173 (M$^+$-1) at RT 3.15 (99.8% purity)

2-Fluoro-N1-(4-fluorobenzyl)-4-nitrobenzene-1,3-diamine (3)

To a stirred suspension of compound 2 (0.100 g, 0.570 mmol, 1.00 equiv) in dry DMSO (4.6 mL) were added 4-fluorobenzylamine (0.210 g, 1.72 mmol, 3.00 equiv) followed by Et$_3$N (69.6 mg, 0.690 mmol, 1.20 equiv) and I$_2$ (catalytic, 1.00 mg). The reaction mixture was heated to 120° C. and stirred at 120° C. for 24 h. After consumption of the starting material (by TLC), the reaction mixture was cooled to RT, diluted with water (25 mL) and extracted with EtOAc (2×25 mL). The separated organic layer was dried over anhydrous Na$_2$SO$_4$, filtered and concentrated under reduced pressure to give crude; which was purified by silica gel column chromatography (EtOAc/Hexane 2:23) to afford compound 3 (0.100 g, 62.5%) as yellow solid. TLC: 20% EtOAc/Hexane ($R_f$: 0.20); $^1$H NMR (400 MHz, CDCl$_3$): δ 7.87 (dd, J=1.60, 9.60 Hz, 1H), 7.31-7.28 (m, 2H), 7.08-7.03 (m, 2H), 6.11-6.03 (m, 3H, 2Exc), 4.82 (br s, 1H, Exc), 4.44 (d, J=5.2 Hz, 2H); LC-MS: m/z=278 (M$^+$-1) at RT 3.64 (91.7% purity)

Ethyl (2-amino-3-fluoro-4-((4-fluorobenzyl)amino)phenyl)carbamate (1A)

To a stirred solution of compound 3 (0.800 g, 2.86 mmol, 1.00 equiv) in methanol (7.2 mL) was added zinc powder (0.930 g, 14.3 mmol, 5.00 equiv) followed by ammonium chloride solution (0.760 g, 14.3 mmol, 5.00 equiv) dropwise. After being stirred at RT for 5 h, DIPEA (0.460 g, 3.58 mmol, 1.25 equiv) and ethyl chloroformate (0.310 g, 2.87 mmol, 1.00 equiv) were added to reaction mixture at 10° C. and the stirring was continued for another 3 h at RT. After consumption of the starting material (by TLC), the reaction mixture was diluted with water (24 mL) and stirred for 1 h to give the solid. The obtained solid was filtered, dissolved in EtOAc (15 mL) and again filtered the un-dissolved solid. The filtrate was evaporated and recrystallized using n-hexane to afford compound 1A (0.250 g, 27.0%) as brown solid. TLC: 50% EtOAc/Hexane ($R_f$: 0.20) $^1$H NMR (500 MHz, CDCl$_3$): δ 7.31 (t, J=7.5 Hz, 2H), 7.02 (t, J=6.8 Hz, 2H), 6.75 (d, J=6.8 Hz, 1H), 6.07 (t, J=6.8 Hz, 1H), 4.31 (s, 2H), 4.22-4.18 (m, 3H), 3.84 (br s, 2H, Exc), 1.29 (t, J=5.6 Hz, 3H); UPLC purity: 91.0%; LC-MS: m/z=322 (M$^+$-1) at RT 3.37 (82.8%)

Example 1B

Synthesis of ethyl (2-amino-6-fluoro-4-((4-fluorobenzyl)amino)phenyl)carbamate (Compound 2A in Table 1)

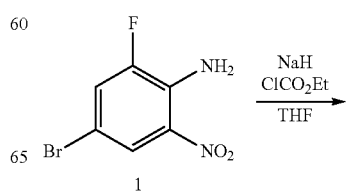

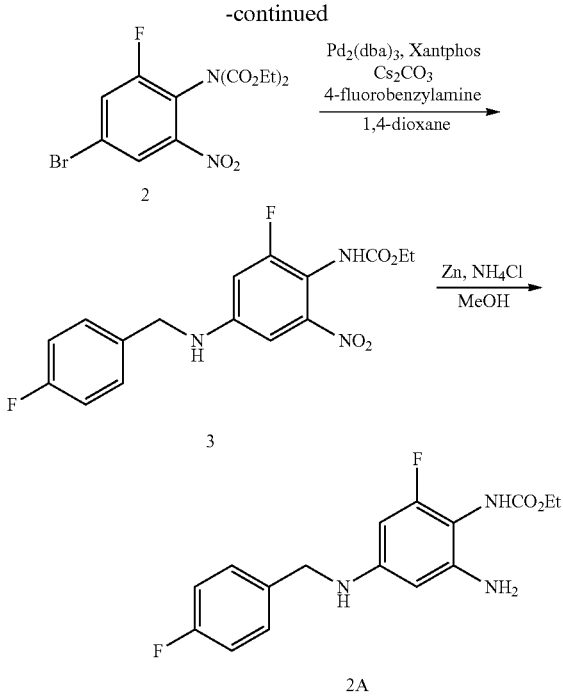

N,N-Bis-ethoxycarbonyl-(4-bromo-2-fluoro-6-nitroaniline) (2)

To a stirred solution of 4-bromo-2-fluoro-6-nitroaniline (1) (0.500 g, 2.12 mmol, 1.00 equiv) in THF (20 mL) was added NaH (0.250 g, 6.40 mmol, 3.00 equiv) portion wise at 0° C. After being stirred for 1 h at RT, ethyl chloroformate (1.00 mL, 10.6 mmol, 5.00 equiv) was added drop wise to the reaction mixture at 0° C. The reaction mixture was heated under reflux temperature for 36 h. After consumption of the starting material (by TLC), the reaction was quenched with saturated NH$_4$Cl solution and extracted with EtOAc (2×100 mL). The combined organic extracts were dried over anhydrous Na$_2$SO$_4$, filtered and concentrated under reduced pressure to give crude; which was purified by silica gel column chromatography (EtOAc/Hexane 1:4) to furnish compound 2 (0.350 g, 43.0%) as yellow solid.

TLC: 30% EtOAc/Hexane (R$_f$: 0.40); $^1$H NMR (500 MHz, CDCl$_3$): δ 8.08 (s, 1H), 7.65 (d, J=6.5 Hz, 1H), 4.27 (q, J=7.0 Hz, 4H), 1.25 (t, J=7.0 Hz, 6H).

Ethyl (2-fluoro-4-((4-fluorobenzyl)amino)-6-nitrophenyl)carbamate (3)

To a stirred solution of compound 2 (0.300 g, 0.790 mmol, 1.00 equiv) in 1,4-dioxane (10 mL) were added 4-fluorobenzylamine (0.200 g, 1.58 mmol, 2.00 equiv), Cs$_2$CO$_3$ (0.500 g, 1.50 mmol, 2.00 equiv) followed by Pd$_2$ (dba)$_3$ (0.072 g, 0.079 mmol, 10 mol %) and Xantphos (0.045 g, 0.079 mmol, 10 mol %) at RT. The reaction mixture was heated at 90° C. and stirred at the same temperature for 8 h. After consumption of the starting material (by TLC), the reaction mixture was concentrated under vacuum. The obtained residue was diluted with water (50 mL) and extracted with EtOAc (2×50 mL). The combined organic extracts were dried over anhydrous Na$_2$SO$_4$, filtered and concentrated under vacuum. The crude material was purified by silica gel column chromatography (EtOAc/Hexane 2:23) to afford compound 3 (0.140 g, 50.3%) as yellow solid. TLC: 40% EtOAc/Hexane (R$_f$: 0.25); $^1$H NMR (500 MHz, CDCl$_3$): δ 7.31-7.28 (m, 2H), 7.06 (t, J=8.5 Hz, 1H), 7.00 (s, 2H), 6.91 (br s, 1H), 6.60 (d, J=9.5 Hz, 1H), 4.46 (br s, 1H), 4.31 (d, J=4.4 Hz, 2H), 4.20 (q, J=7.0 Hz, 2H), 1.28 (t, J=7.0 Hz, 3H); LC-MS: m/z=350 (M$^+$-1) at RT 3.69 (97.8% purity).

Ethyl (2-amino-6-fluoro-4-((4-fluorobenzyl)amino)phenyl)carbamate (2A)

To a stirred solution of compound 3 (0.075 g, 0.24 mmol, 1.0 equiv) in methanol (3 mL) was added zinc powder (0.0800 g, 1.22 mmol, 5.00 equiv) followed by ammonium chloride solution (0.065 g, 1.2 mmol, 5.0 equiv) in water (1 mL). The reaction mixture was stirred at RT for 4 h. After consumption of the starting material (by TLC), the reaction mixture was diluted with DCM (10 mL), water (10 mL) and filtered through a pad of celite. The organic layer was separated from filtrate and the aqueous layer was extracted with DCM (2×10 mL). The combined organic extracts were dried over anhydrous Na$_2$SO$_4$, concentrated under vacuum to give crude; which was purified by silica gel column chromatography (EtOAc/Hexane, 1:4) to afford compound 2A (0.050 g, 71%) as an off-white solid. TLC: 40% EtOAc/Hexane (R$_f$: 0.20); $^1$H NMR (400 MHz, CDCl$_3$): δ 7.32-7.29 (m, 2H), 7.04 (t, J=8.8 Hz, 2H), 5.84 (d, J=9.6 Hz, 1H), 5.78 (s, 1H), 4.25-4.18 (m, 4H), 4.04-3.96 (m, 3H), 1.30 (t, J=6.8 Hz, 3H); LC-MS: m/z=322 (M$^+$+1) at RT 3.38 (99.0% purity); UPLC purity: 99.5%.

Example 1C

Synthesis of ethyl (2-amino-5-fluoro-4-((4-fluorobenzyl)amino)phenyl)carbamate (Compound 3A in table 1)

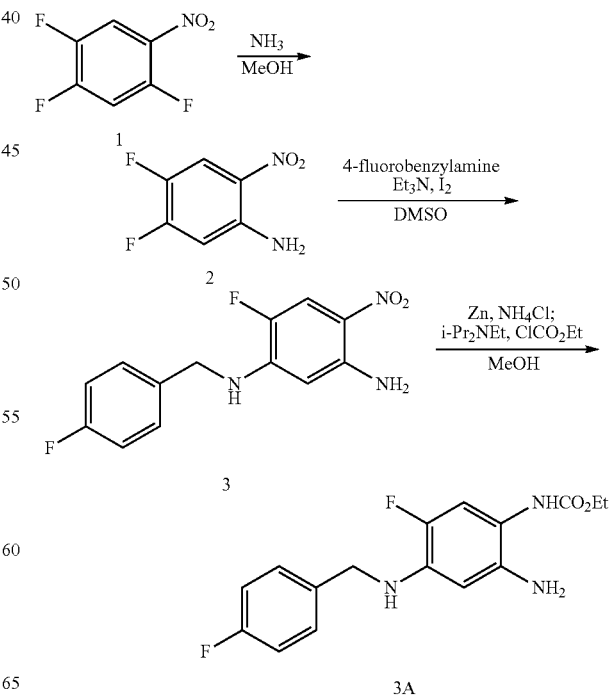

4,5-Difluoro-2-nitroaniline (2)

To a solution of 1,2,4-trifluoro-5-nitrobenzene (1) (5.00 g, 28.0 mmol, 1.00 equiv) in methanol (5 mL) was added methanolic ammonia (15 mL) and taken in microwave vial. The reaction mixture was heated in microwave at 70° C. for 90 min. The reaction mixture was cooled to RT and removed the solvent from the reaction under reduced pressure to give crude; which was purified by silica gel column chromatography (EtOAc/Hexane 1:4) to furnish compound 2 (0.600 g, 12.0%) as yellow solid. TLC: 30% EtOAc/Hexane ($R_f$: 0.35); $^1$H NMR (500 MHz, CDCl$_3$): δ 8.00 (t, J=9.0 Hz, 1H), 6.65-6.58 (m, 1H), 6.08 (br s, 2H).

6-Fluoro-N1-(4-fluorobenzyl)-4-nitrobenzene-1,3-diamine (3)

To a stirred suspension of compound 2 (0.600 g, 3.40 mmol, 1.00 equiv) in dry DMSO (15 mL) was added 4-fluorobenzylamine (1.20 g, 10.0 mmol, 3.00 equiv) followed by Et$_3$N (0.500 mL, 4.10 mmol, 1.20 equiv) and I$_2$ (catalytic, 1.00 mg). The reaction mixture was heated to 120° C. and stirred at 120° C. for 16 h. After consumption of the starting material (by TLC), the reaction mixture was cooled to RT, diluted with water (25 mL) and extracted with EtOAc (2×50 mL). The separated organic layer was dried over anhydrous Na$_2$SO$_4$, filtered and concentrated under reduced pressure to give crude; which was purified by silica gel column chromatography (EtOAc/Hexane 2:3) to afford compound 3 (0.550 g, 52.0%) as yellow solid. TLC: 70% EtOAc/Hexane ($R_f$: 0.20); $^1$H NMR (400 MHz, DMSO-d$_6$): δ 7.60-7.54 (m, 2H), 7.38-7.32 (m, 4H), 7.17 (t, J=8.8 Hz, 2H), 5.92 (d, J=8.0 Hz, 1H), 4.33 (d, J=6.0 Hz, 2H); LC-MS: m/z=278 (M$^+$-1) at RT 3.59 (99.4% purity).

Ethyl (2-amino-5-fluoro-4-((4-fluorobenzyl)amino) phenyl)carbamate (3A)

To a stirred solution of compound 3 (0.400 g, 1.40 mmol, 1.00 equiv) in methanol (10 mL) was added zinc powder (0.470 g, 7.10 mmol, 5.00 equiv) followed by ammonium chloride solution (0.380 g, 9.10 mmol, 5.00 equiv) drop wise. After being stirred for 5 h at RT, DIPEA (0.155 g, 1.54 mmol, 1.10 equiv) and ethyl chloroformate (0.151 g, 1.40 mmol, 1.00 equiv) were added to reaction mixture at 0° C. and the stirring was continued for another 3 h at RT. After consumption of the starting material (by TLC), the reaction mixture was diluted with water (25 mL) and Extracted with EtOAc (2×75 mL). The separated organic layer was dried over anhydrous Na$_2$SO$_4$, filtered and concentrated under reduced pressure to give crude; which was purified by silica gel column chromatography (EtOAc/Hexane 1:4) to afford to compound 3A (0.100 g, 21.0%) as brown solid. TLC: 40% EtOAc/Hexane ($R_f$: 0.50); $^1$HNMR (400 MHz, DMSO-d$_6$): δ 8.27 (br s, 1H), 7.39-7.34 (m, 2H), 7.12 (t, J=8.8 Hz, 2H), 6.81-6.78 (m, 1H), 5.93 (d, J=9.2 Hz, 1H), 5.79 (t, J=6.4 Hz, 1H), 4.42 (s, 2H), 4.22 (d, J=6.0 Hz, 2H), 4.03 (q, J=6.8 Hz, 2H), 1.19 (t, J=6.8 Hz, 3H); LC-MS: m/z=322 (M$^+$+1) at RT 3.54 (95.8% purity); UPLC purity: 98.8%

Example 1D

Synthesis of ethyl (2-amino-3,5-difluoro-4-((4-fluorobenzyl)amino)phenyl)carbamate (Compound 4A in Table 1)

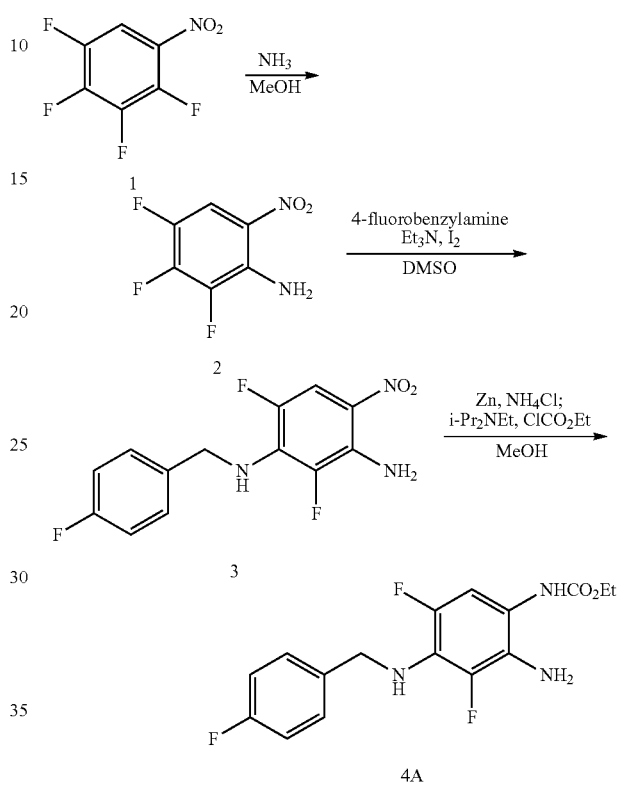

2,3,4-Trifluoro-6-nitroaniline (2)

A solution of 1,2,3,4-tetrafluoro-5-nitrobenzene (1) (1.50 g, 7.69 mmol, 1.00 equiv) and NH$_3$ in THF (3 mL) was taken in a sealed tube and stirred at RT for 16 h. After 16 h, TLC monitoring indicated the presence of unreacted starting material and formation of the desired product. The solvent from the reaction was removed under reduced pressure to give crude; which was purified by silica gel column chromatography (EtOAc/Hexane 1:19) to furnish compound 2 (0.200 g, 14.0%) as yellow solid. TLC: 20% EtOAc/Hexane ($R_f$: 0.45); $^1$H NMR (400 MHz, CDCl$_3$): δ 7.88-7.83 (m, 1H), 6.10 (br s, 2H, Exc); LC-MS: m/z=191 (M$^+$-1) at RT 3.14 (99.4% purity)

2,6-Difluoro-N1-(4-fluorobenzyl)-4-nitrobenzene-1,3-diamine (3)

To a stirred suspension of compound 2 (0.060 g, 0.31 mmol, 1.0 equiv) in dry DMSO (0.3 mL) was added 4-fluorobenzylamine (0.117 g, 0.940 mmol, 3.00 equiv) followed by Et$_3$N (54.0 μL, 0.370 mmol, 1.20 equiv) and I$_2$ (catalytic, 1.0 mg). The reaction mixture was heated to 120° C. and stirred at 120° C. for 16 h. After consumption of the starting material (by TLC), the reaction mixture was cooled to RT, diluted with water (25 mL) and extracted with EtOAc (2×50 mL). The separated organic layer was dried over anhydrous Na$_2$SO$_4$, filtered and concentrated under reduced pressure to give crude; which was purified by silica gel column chromatography (EtOAc/Hexane 2:23) to afford compound 3 (0.064 g, 69%) as yellow solid. TLC: 25% EtOAc/Hexane (R$_f$: 0.20); $^1$H NMR (400 MHz, CDCl$_3$): δ 7.67 (dd, J=2.0, 12.8 Hz, 1H), 7.31-7.28 (m, 2H), 7.05 (t, J=6.8 Hz, 2H), 6.05 (br s, 2H, Exc), 4.63 (d, J=6.0 Hz, 2H), 4.53 (br s, 1H, Exc); LC-MS: m/z=296 (M$^+$-1) at RT 3.64 (98.8% purity)

Ethyl (2-amino-3,5-difluoro-4-((4-fluorobenzyl)amino)phenyl)carbamate (4A)

To a stirred solution of compound 3 (0.062 g, 0.21 mmol, 1.0 equiv) in methanol (0.560 mL) was added zinc powder (0.068 g, 1.04 mmol, 5.00 equiv) followed by ammonium chloride solution (55.3 mg, 1.04 mmol, 5.00 equiv) dropwise. After being stirred for 4 h at RT, DIPEA (48.0 μL, 0.260 mmol, 1.25 equiv) and ethyl chloroformate (20.0 μL, 0.210 mmol, 1.00 equiv) were added to reaction mixture at 10° C. and the stirring was continued for another 2 h at RT. After consumption of the starting material (by TLC), the reaction mixture was diluted with water (25 mL) and extracted with EtOAc (2×75 mL). The separated organic layer was dried over anhydrous Na$_2$SO$_4$, filtered and concentrated under reduced pressure to give crude; which was purified by neutral alumina column chromatography (EtOAc/Hexane 18:82) to afford to compound 4A (0.017 g, 21%) as an off-white solid. TLC: 50% EtOAc/Hexane (R$_f$: 0.50); $^1$H NMR (500 MHz, CDCl$_3$): δ 7.30-7.27 (m, 2H), 7.00 (t, J=8.5 Hz, 2H), 6.88 (d, J=11.5 Hz, 1H), 6.26 (br s, 1H, Exc), 4.40 (d, J=6.0 Hz, 2H), 4.21 (q, J=7.0 Hz, 2H), 3.75 (br s, 1H, Exc), 3.50 (s, 2H, Exc), 1.30 (t, J=7.0 Hz, 3H); LC-MS: m/z=340 (M$^+$+1) at RT 3.46 (94.3% purity); UPLC purity: 95.2%

Example 1E

Synthesis of ethyl-d5 (2-amino-3-fluoro-4-((4-fluorobenzyl)amino)phenyl)carbamate (Compound 10A in Table 3)

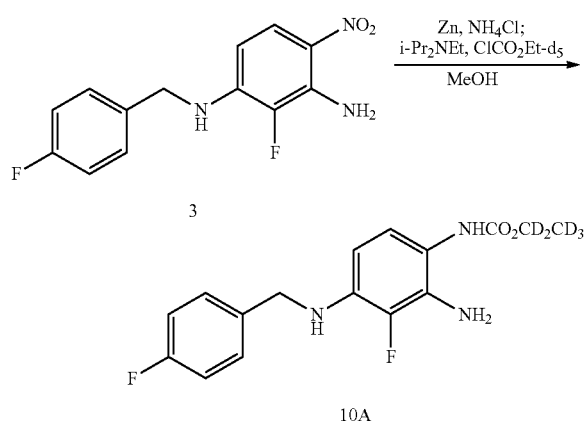

To a stirred solution of compound 3 (1.00 equiv), prepared as in Example 1A, in methanol (7.2 mL) is added zinc powder (5.00 equiv) followed by ammonium chloride solution (5.00 equiv) dropwise. After stirring at RT for 5 h, DIPEA (1.25 equiv) and ethyl-d5 chloroformate (1.00 equiv) are added to the reaction mixture at 10° C. and the stirring is continued for another 3 h at RT. After consumption of the starting material (by TLC), the reaction mixture is diluted with water (24 mL) and stirred for 1 h to give the solid. The obtained solid is filtered, dissolved in EtOAc (15 mL) and again filtered to remove the un-dissolved solid. The filtrate is evaporated and recrystallized using n-hexane to afford compound 10A.

Example 2

Experimental Procedures for 18F Compounds

Example 2A

Synthesis of [$^{18}$F]-ethyl (2-amino-4-((4-fluorobenzyl)amino)phenyl)carbamate ([$^{18}$F]-Ezogabine) (Compound 5A in Table 2)

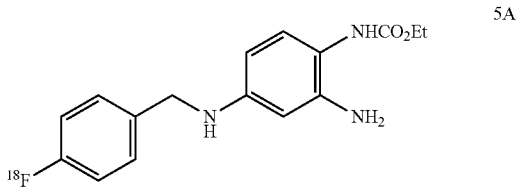

3-Fluoro-6-nitroaniline

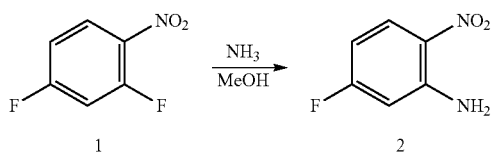

A solution of 1,3-difluoro-4-nitrobenzene (1) (1.59 g, 10.0 mmol, 1.00 equiv) in methanolic ammonia (1.5 mL) is taken in microwave vial and heated to 70° C. for 90 min in a microwave. The solvent is evaporated under vacuum to give a crude mixture, which is purified by silica gel column chromatography (Ethyl acetate/Hexane) to furnish the desired product.

N1-(4-phenylboronic acid methyl)-4-nitrobenzene-1,3-diamine (3)

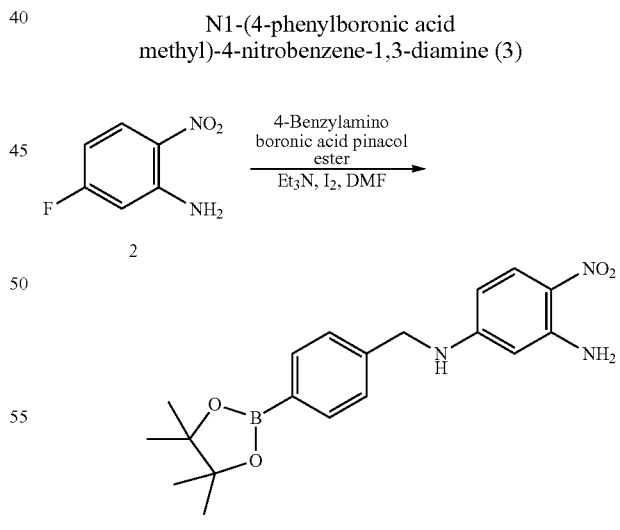

A round bottom flask is charged with 3-fluoro-6-nitroaniline (2) (1.00 g, 6.40 mmol, 1.00 equiv) and 4-Phenylboronic acid pinacolester (4.47 g, 19.2 mmol, 3.00 equiv). Dry DMF (25 mL) is then added followed by Et$_3$N (0.775 g, 7.68 mmol, 1.20 equiv) and I$_2$ (catalytic, 1.00 mg). The reaction mixture is heated to 120° C. and stirred at 120° C. for 24 h.

The reaction mixture is then cooled to RT, diluted with water (75 mL) and extracted with Ethyl acetate (2×60 mL). The organic layer is dried over anhydrous $Na_2SO_4$, filtered and concentrated under reduced pressure to give crude material, which is purified by silica gel column chromatography (Hexane/Hexane) to afford compound 3 as the desired product.

Ethyl (2-amino-4-((4-benzylboronicacid pinacolester)amino)phenyl)carbamate (4)

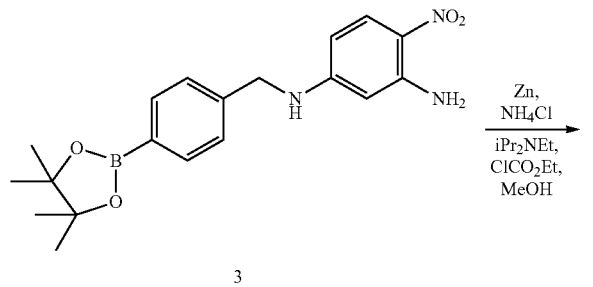

To a stirred solution of compound 3 (1.00 g, 2.71 mmol, 1.00 equiv) in methanol (7 mL) is added zinc powder (0.888 g, 13.5 mmol, 5.00 equiv) followed by ammonium chloride solution (0.725 g, 13.55 mmol, 5.00 equiv) dropwise. After 5 h, DIPEA (0.436 g, 3.38 mmol, 1.25 equiv) and ethyl chloroformate (0.292 g, 2.71 mmol, 1.00 equiv) are added to reaction mixture at 10° C. and the stirring is continued till consumption of starting material (by TLC). The reaction mixture is diluted with water (24 mL) and extracted in ethyl acetate (75 mL), dried using brine and over MgSO4. After concentration the crude material obtained is purified to afford the title compound.

Ethyl (2-tertbutoxycarbonylamino-4-((4-benzylboronicacid pinacolester)tertbutoxycarbonyl amino)phenyl)carbamate (5)

To a round bottom flask is charged 4 (1.00 g, 2.45 mmol, 1.00 equiv) and the compound is dissolved in dichloromethane. Boc anhydride (1.175 g, 5.39 mmol, 2.2 equiv) is then added to it and the reaction mixture is stirred at room temperature for 16 hours. The reaction mixture is concentrated and the residue is purified by silica gel column chromatography (Hexane/Hexane) to afford compound 5 as the desired product.

Palladium Complex 6

To the palladium complex A (550 mg, 0.996 mmol, 1.00 equiv), synthesized according to Ritter et. al., (*Science*, 2011, 334, 639-642) in MeOH (5.0 mL) and benzene (5.0 mL) at 23° C. is added 5 (527 mg, 1.29 mmol, 1.3 equiv) and $K_2CO_3$ (206 mg, 1.494 mmol, 1.5 equiv). The reaction mixture is stirred at 23° C. for 10 hours after which it is diluted with $CH_2Cl_2$ (80 mL), filtered through Celite and eluted with additional $CH_2Cl_2$ (30 mL). The solution is then washed with water (3×20 mL) and dried over $Na_2SO_4$ and concentrated. The residue obtained is then recrystallized using $CH_2Cl_2$/pentane to afford the desired compound 6.

[18F]-Ezogabine

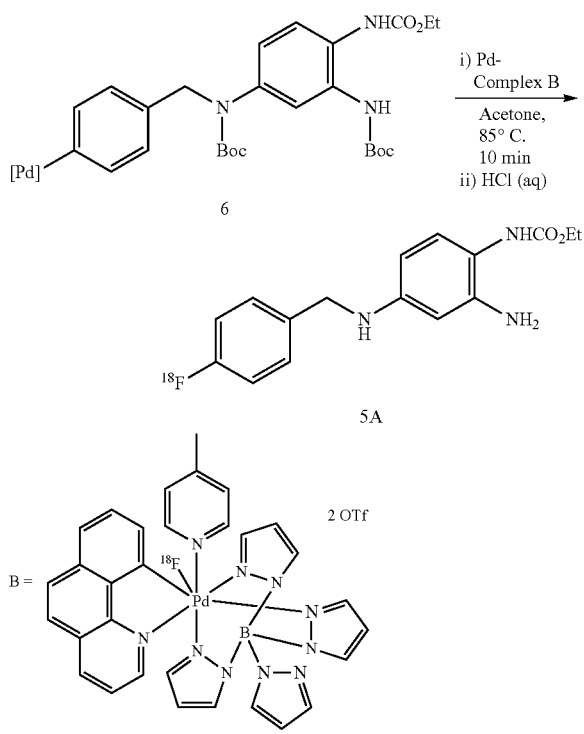

To the palladium complex B, prepared according to Ritter et. al., (*Science*, 2011, 334, 639-642) in 1.5 mL acetone is added 6 and the mixture heated to 85 C. for 10 minutes in a securely capped vial. The vial is cooled and the resulting solution purified via HPLC to obtain the desired compound 5A (Table 2).

Example 2B

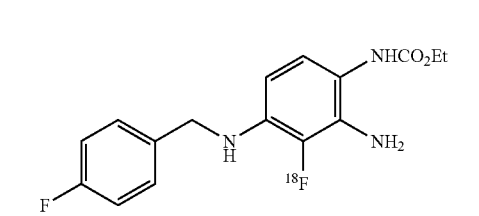

1-fluoro-2,4-dinitro-3-amino benzene (8)

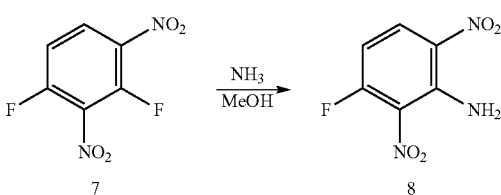

A solution of 1,3-difluoro-2,4-nitrobenzene (7) (2.04 g, 10.0 mmol, 1.00 equiv) in methanolic ammonia (3.0 mL) is taken in microwave vial and heated to 70° C. for 90 min in a microwave. The solvent is evaporated under vacuum to give a crude mixture, which is purified by silica gel column chromatography (Hexane/Hexane) to furnish the desired product 8.

1,3-dinitro-2-amino-4-(4-fluorobenzyl)amino benzene (9)

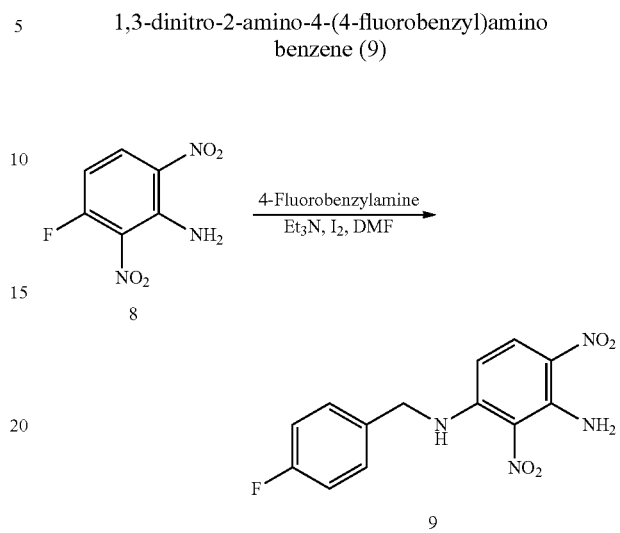

A round bottom flask is charged with 8 (2.01 g, 10 mmol, 1 equiv), 4-fluorobenzylamine (3.79 g, 30 mmol, 3 equiv) and triethylamine (1.21 g, 12 mmol, 1.2 equiv). DMF (40 mL) is then added to the above mixture followed by iodine (catalytic, 1 mg). The reaction mixture is then heated to 120° C. and stirred at 120° C. for 16 hrs after which the flask is allowed to cool to room temperature. The reaction mixture is diluted with ethyl acetate and washed with water (5×80 mL) and dried with brine and then over MgSO$_4$. The suspension is filtered and concentrated to give a residue, which is purified by silica gel flash chromatography (hexanes/ethyl acetate) to give the desired product (9).

Ethyl (2-amino-3-nitro-4-((4-fluorobenzyl)amino)phenyl)carbamate (10)

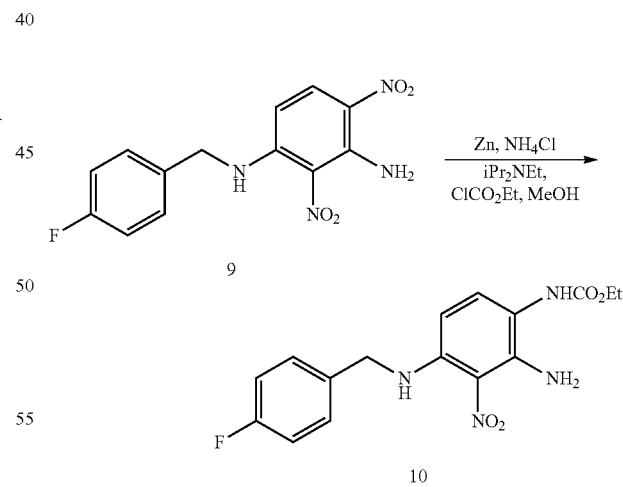

To a stirred solution of compound 9 (1.5 g, 5 mmol, 1.00 equiv) in methanol (7 mL) is added zinc powder (1.64 g, 25 mmol, 5.00 equiv) followed by ammonium chloride solution (1.33 g, 25 mmol, 5.00 equiv) dropwise. After 5 h, DIPEA (0.806 g, 6.25 mmol, 1.25 equiv) and ethyl chloroformate (0.54 g, 5 mmol, 1.00 equiv) are added to reaction mixture at 10° C. and the stirring continued till consumption of starting material (by TLC). The reaction mixture is diluted with water (30 mL) and extracted in ethyl acetate (75 mL), dried using brine and over MgSO$_4$. After concentration the crude material obtained is purified to afford the title compound.

Ethyl (2-amino-3-[$^{18}$F]fluoro-4-((4-fluorobenzyl)amino)phenyl)carbamate ([$^{18}$F] Fluoro Ezogabine)

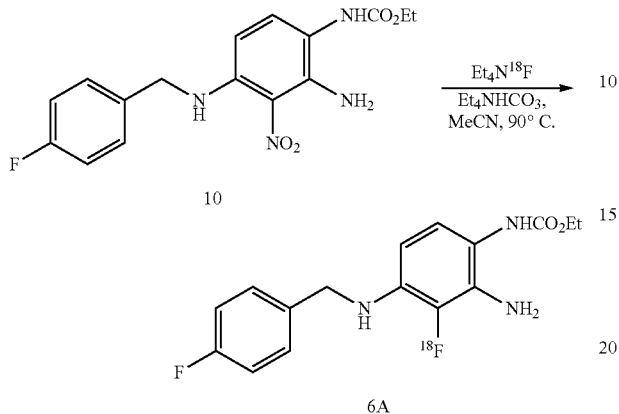

$^{18}$F deposited on an ORTG/QMA anion exchange column is eluted with a solution of Et$_4$NHCO$_3$ in a 4 mL reaction vial. The resulting solution is dried over nitrogen and heat (110° C.). The resulting residue is then dried twice azeotropically using acetonitrile at 95° C. with nitrogen flow. A solution of 10 in 1 mL acetonitrile (anhydrous) is then added and the vial securely capped and heated to 110° C. for 10 minutes in a heating block. After cooling to room temperature the solution is reconstituted as appropriate and purified to obtain the desired compound 6A (Table 2).

Example 2C

[$^{18}$F] Flupirtine

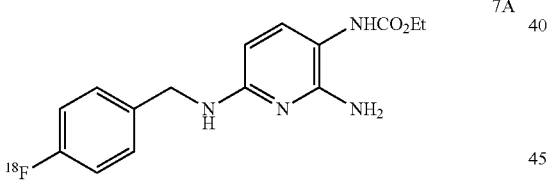

The preparation of 18F-flupirtine (compound 7A, Table 2) is performed using the same procedure as described in Example 2A, substituting 2,6-difluoro-3-nitropyridine for 1,3-difluoro-4-nitrobenzene.

Example 2D

[$^{18}$F] Fluoroflupirtine

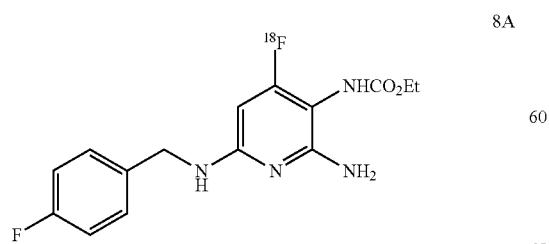

The preparation of 18F-Fluoroflupirtine (compound 8A, Table 2) is performed using the same procedure as described in Example 2B, substituting 2,6-difluoro-3,4-dinitropyridine for 1,3-difluoro-2,4-nitrobenzene.

Example 2E

Synthesis of ethyl (2-amino-3-fluoro-4-((4-[$^{18}$F]fluorobenzyl)amino)phenyl)carbamate (Compound 9A in Table 2)

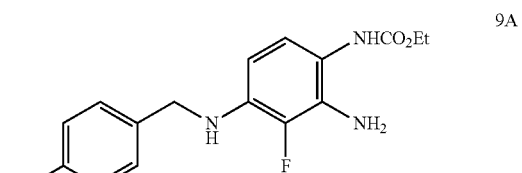

Synthesis of 2,3-difluoro-6-nitroaniline (2)

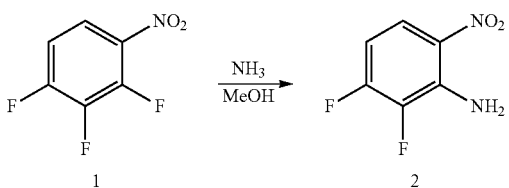

A solution of 1,2,3-trifluoro-4-nitrobenzene (1) (1.0 g, 5.6 mmol, 1.00 equiv.) in freshly prepared methanolic ammonia (3 mL) was charged to a microwave vial and heated to 70° C. for 90 min in a microwave. The solvent was evaporated under reduced pressure to give a crude mixture, which was purified by silica gel column chromatography (Ethyl acetate/Hexane) to furnish the desired product (2, 0.85 gm, 81%).

Synthesis of 2-fluoro-3-(4-bromobenzyl)-6-nitroaniline (3)

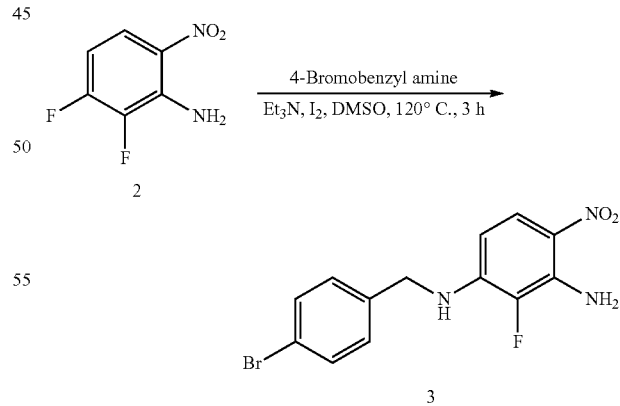

A round bottom flask was charged with 2,3-difluoro-6-nitroaniline (0.50 g, 2.87 mmol, 1.00 equiv.) and 4-bromobenzylamine (0.959 g, 5.15 mmol, 1.80 equiv.). Dimethyl sulfoxide (2.5 mL) was then added flowed by Et$_3$N (0.968 mL, 6.88 mmol, 2.40 equiv.) and I$_2$ (catalytic, 10 mg). The reaction mixture was heated to 120° C. and stirred for 3 h. The reaction mixture was then cooled to ambient temperature, diluted with water (75 mL) and extracted with Ethyl acetate (2×60 mL). The organic layer was dried over anhydrous Na$_2$SO$_4$, filtered and concentrated under reduced pressure to give crude material, which was purified by silica gel column chromatography (10% ethyl acetate/hexane) to afford compound 3 as the desired product (0.869 g, 89%).

Synthesis of Ethyl (2-amino-3-fluoro-4-((4-bromobenzyl)amino)phenyl)carbamate (4)

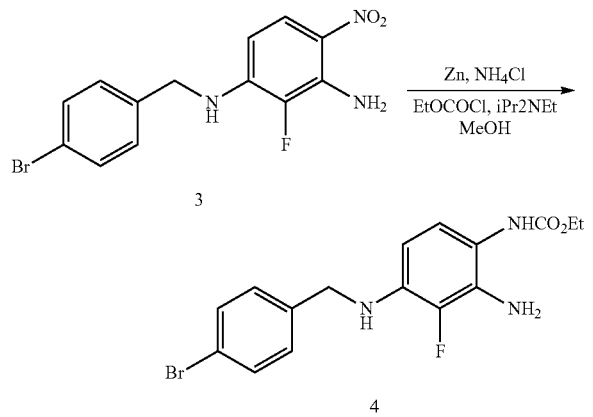

To a stirred solution of compound 3 (0.90 g, 2.64 mmol, 1.00 equiv.) in methanol (7.9 mL) was added zinc powder (0.864 g, 13.2 mmol, 5.00 equiv.) followed by ammonium chloride solution (0.706 g, 13.2 mmol, 5.00 equiv.) drop wise. After 5 h, DIPEA (0.426 g, 3.3 mmol, 1.25 equiv.) and ethyl chloroformate (0.286 g, 2.64 mmol, 1.00 equiv.) were added to the reaction mixture at 10° C. and the stirring was continued at room temperature for 3 hours. The reaction mixture was diluted with water (24 mL) and extracted in ethyl acetate (75 mL), washed with brine and dried over MgSO4. After concentration the crude material obtained was purified by silica gel column chromatography to afford compound 4 (510 mg, 50%).

Synthesis of Ethyl (2-$^t$butoxycarbonylamino-3-fluoro-4-((4-bromobenzyl) $^t$butoxycarbonylamino)phenyl)carbamate (5)

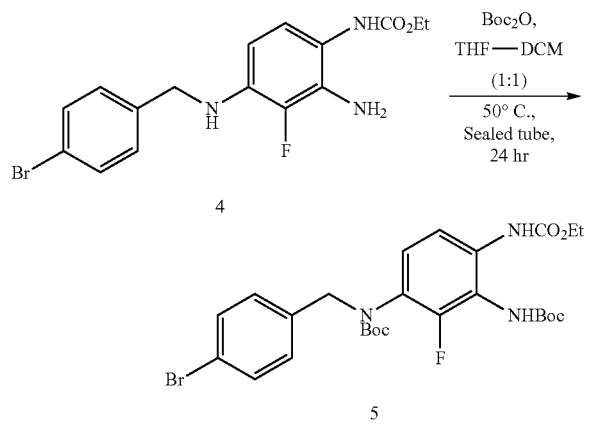

To a heavy walled glass tube charged with 4 (0.50 g, 1.3 mmol, 1.00 equiv.) was added 5 mL of THF:DCM (1:1) followed by addition of Boc anhydride (0.85 g, 3.9 mmol, 3.0 equiv.). The tube was then sealed and heated to 50° C. for 24 hours. After cooling to room temperature the mixture was concentrated and taken up in ethyl acetate, washed with water and dried over MgSO$_4$. Concentration of the solution gave a residue that was purified by silica gel chromatography (hexanes:ethylacetate) to give compound 5 (420 mg, 55%).

Synthesis of Ethyl (2-$^t$butoxycarbonylamino-3-fluoro-4-((4-(1,3,2-dioxoborolan-2-yl)benzyl) $^t$butoxycarbonylamino)phenyl)carbamate (6)

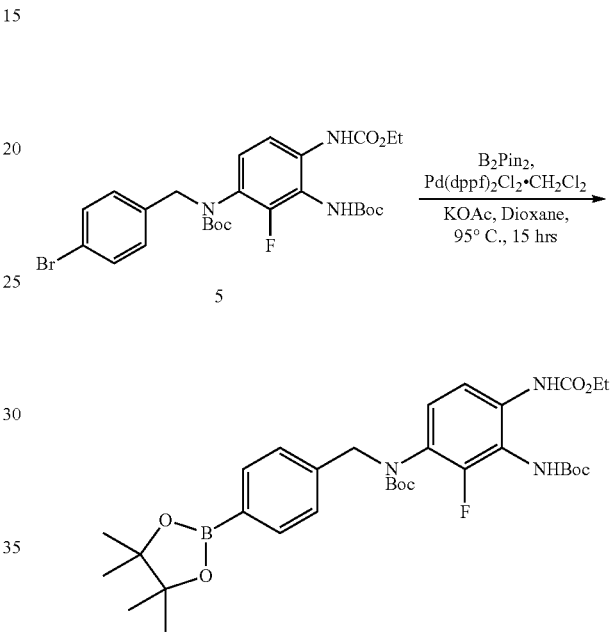

To a 20 mL vial was charged 5 (380 mg, 0.65 mmol), bispinacolatodiboron (198 mg, 0.78 mmol, 1.2 equiv.), potassium acetate (192 mg, 1.95 mmol, 3 equiv.) and Pd(dppf)Cl$_2$.CH$_2$Cl$_2$ (23.7 mg, 0.032 mmol, 0.05 equiv.). Dioxane was then added and the reaction stirred at 95° C. for 12 hours under nitrogen. The reaction mixture was then concentrated and filtered through a pad of silica eluting with 1:1 hexanes:ethylacetate (200 mL). The clear and colorless filtrate was then concentrated and purified using silica gel chromatography (hexanes:ethylacetate) to give compound 6 (260 mg, 63%).

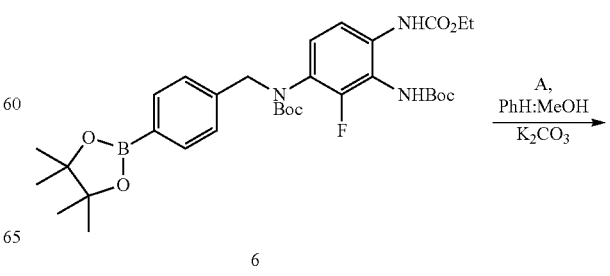

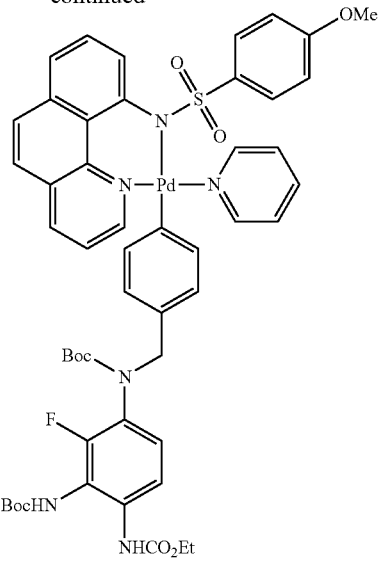

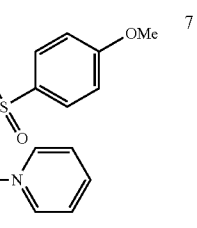

A =

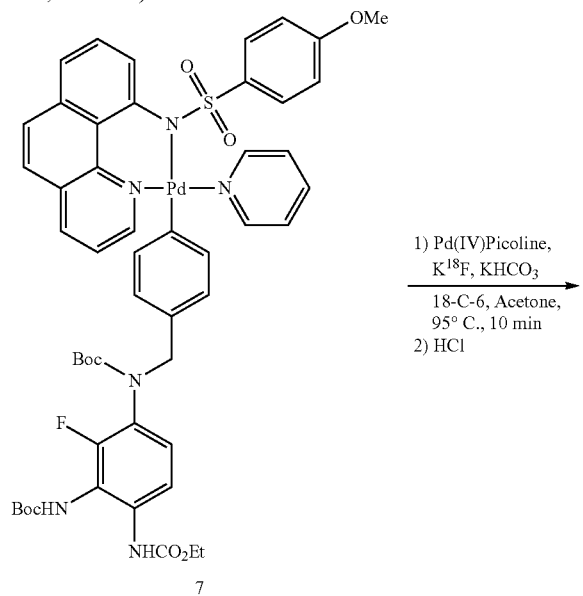

1) Pd(IV)Picoline, K$^{18}$F, KHCO$_3$
18-C-6, Acetone, 95° C., 10 min
2) HCl

To a 20 ml vial was charged 6 (240 mg, 0.38 mmol) and A (232 mg, 0.38 mmol, 1 equiv.). 7.6 ml of 1:1 benzene:methanol was then added followed by potassium carbonate (79 mg, 0.57 mmol, 1.5 equiv.). The reaction solution was stirred for 22 hours after which it was concentrated, re-dissolved in dichloromethane and filtered through a pad of celite eluting with dichloromethane (40 mL). The filtrate was concentrated and purified by silica gel chromatography (hexanes:ethyl acetate) to obtain compound 7 as a yellow solid (230 mg, 58%). NOTE: Compound A shown above was synthesized according to published procedure (Lee et. al., Science, 2011, 334, 639-642)

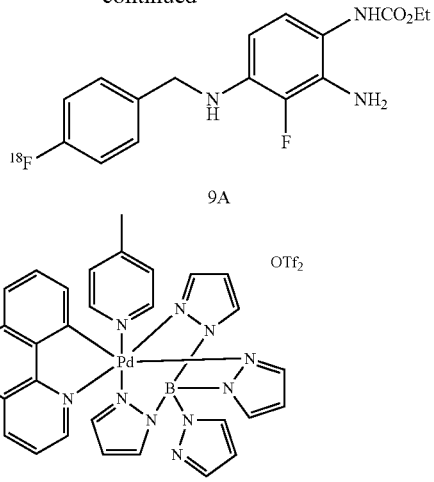

Pd(IV)Picoline:

$^{18}$F (as $^{18}$O water) obtained from PETNET (Woburn, Mass.) was first trapped on a QMA Light cartridge (Waters, Milford, Mass.) that was previously conditioned with 10 mL of 4 mg/mL KHCO$_3$ solution followed by 10 mL of water. The $^{18}$F trapped was then eluted with 0.5 ml of 2 mg/mL KHCO$_3$ solution and the cartridge washed with 0.5 mL of 18C6 solution in acetonitrile (26.2 mg/ml) into a 5 mL Wheaton Reacti-Vial. The vial was then inserted into a heating block at 110° C. for drying under a stream of nitrogen. An additional 1 ml acetonitrile was used for drying after which a white residue was seen on the walls of the vial. This was followed by an acetone exchange step in which 0.5 ml of acetone was added and removed under a constant stream of nitrogen without heating. A glassy film along the sides and a viscous liquid at the bottom of the vial were obtained at the end of this process (approximately 15 min total time). A stir bar was then introduced and the vial quickly capped while being flushed with nitrogen.

Pd(IV)Picoline (10 mg) contained in a sealed nitrogen filled vial, was dissolved in acetone (0.5-0.6 mL) and added to the above vial containing dried $^{18}$F. This mixture was stirred vigorously for 10 minutes after which the cap was opened and the solution filtered through a pipette containing JandaJel™-Polypyridine (20-30 mg) followed by rinsing with additional 0.5 ml of acetone into a vial containing compound 7 (4-5 mg). This vial was then heated to 85° C. for 10 minutes after which analysis by radio-TLC indicated 37% conversion. The acetone was then evaporated and 0.5 ml of hexanes:ethyl acetate (1:1) was added. This was then passed through a pipette containing silica followed by elution with additional 1-1.5 ml hexanes:ethyl acetate (1:1). The hexanes:ethyl acetate solution was then evaporated to dryness and concentrated HCl (0.5 mL) was added. The vial was then heated to 85° C. for 5 minutes followed by reconstitution to 2 ml of 1:1 MeCN:Water followed by purification on the Semi Prep HPLC (4.6×10 mm Xterra MS C$_{18}$, 6:4 MeCN:Water with 0.1% formic acid; 5 ml/min) to get the desired product. The retention time of 9A matched that for the corresponding $^{19}$F compound.

NOTE: Pd(IV)Picoline was synthesized according to published procedure ((Lee et. al., Science, 2011, 334, 639-642).

Example 3

Assessment of KCNQ2/3 Channel Activation Activity

The in vitro effects of ezogabine and Compound 1A on cloned KCNQ2/3 potassium channels (encoded by the human KCNQ2/3 gene and expressed in HEK293 cells) were evaluated at room temperature using the QPatch HT® (Sophion Bioscience A/S, Denmark), an automatic parallel patch clamp system. Each test article was evaluated at 0.01, 0.1, 1, 10 and 100 μM with each concentration tested in at least two cells (n≥2). The duration of exposure to each test article concentration was 5 minutes.

The baseline for each recording was established using a 5-10 minute vehicle application (HBPS+0.3% DMSO). A single test article concentration was applied for a period of 5 minutes after the vehicle, followed by a 3 minute application of 30 μM flupirtine. Each recording ended with a supramaximal dose of 30 μM linopirdine. A summary of the results is shown in Table 4. The % activation was calculated using the following equation by using leak subtracted responses:

$$\frac{vehicle\_response - compound\_response}{vehicle\_response - flupirtine\_response}$$

TABLE 4

| Test Article ID | Conc (μM) | Mean % KCNQ2/3 Activation | Standard Deviation | Standard Error | n | Individual Data Points (% Activation) |
|---|---|---|---|---|---|---|
| ezogabine | 0.01 | 6.6 | 6.4 | 4.5 | 2 | 2.1 |
|  |  |  |  |  |  | 11.1 |
|  | 0.1 | 40.6 | 11.9 | 8.4 | 2 | 32.2 |
|  |  |  |  |  |  | 49.1 |
|  | 1 | 94.4 | 1.1 | 0.8 | 2 | 93.6 |
|  |  |  |  |  |  | 95.2 |
|  | 10 | 132.0 | 11.8 | 8.3 | 2 | 123.7 |
|  |  |  |  |  |  | 140.4 |
|  | 100 | 104.1 | 11.5 | 6.6 | 3 | 93.8 |
|  |  |  |  |  |  | 101.9 |
|  |  |  |  |  |  | 116.5 |
| Compound 1A | 0.01 | 31.4 | 6.3 | 4.5 | 2 | 35.9 |
|  |  |  |  |  |  | 26.9 |
|  | 0.1 | 62.9 | 31.2 | 18.0 | 3 | 98.9 |
|  |  |  |  |  |  | 43.3 |
|  |  |  |  |  |  | 46.6 |
|  | 1 | 125.5 | 2.9 | 2.0 | 2 | 123.5 |
|  |  |  |  |  |  | 127.6 |
|  | 10 | 119.9 | 0.3 | 0.2 | 2 | 119.7 |
|  |  |  |  |  |  | 120.1 |
|  | 100 | 61.9 | 7.5 | 5.3 | 2 | 56.6 |
|  |  |  |  |  |  | 67.3 |

Compounds of the present invention 2A, 3A, and 4A were tested in this assay at a single concentration (0.1 μM) and were found to be equivalent in activity to ezogabine.

What is claimed:

1. A compound, which is

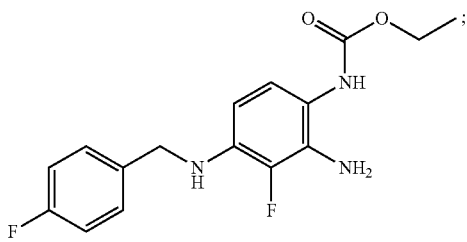 [SMILES: CCOC(=O)Nc1ccc(NCc2ccc(F)cc2)c(F)c1N ; ";"]

or a pharmaceutically acceptable salt or solvate thereof.

2. A pharmaceutical composition comprising the compound of claim 1 or a pharmaceutically acceptable salt or solvate thereof and one or more pharmaceutically acceptable carrier or excipient.

3. A method of treating a subject suffering from or susceptible to conditions ameliorated by KCNQ2/3 potassium channel opening, comprising administering to the subject an effective amount of the compound of claim 1 or a pharmaceutically acceptable salt or solvate thereof.

4. A method of treating or preventing a disease or disorder selected from epilepsy, neurodegenerative disorder, CNS disorder, neurotransmission disorder, cognitive disorder, cancer, inflammatory disease, ophthalmic disease, migraine, bipolar disorder, unipolar depression, anxiety disorder, functional bowel disorder, and tinnitus in a subject in need thereof, comprising administering to the subject an effective amount of the compound of claim 1 or a pharmaceutically acceptable salt or solvate thereof.

5. The method of claim 4, wherein the disease is epilepsy.

6. A method of producing an analgesic effect in a subject in need thereof, comprising administering to the subject an effective amount of the compound of claim 1 or a pharmaceutically acceptable salt or solvate thereof.

* * * * *